(12) United States Patent
Ayabe et al.

(10) Patent No.: US 7,462,478 B2
(45) Date of Patent: Dec. 9, 2008

(54) POLYNUCLEOTIDE ENCODING 2-HYDROXYISOFLAVANONE DEHYDRATASE AND APPLICATION OF THE SAME

(75) Inventors: Shin-ichi Ayabe, Tokyo (JP); Tomoyoshi Akashi, Tokyo (JP); Toshio Aoki, Tokyo (JP)

(73) Assignee: Nihon University, Tokyo (JP)

( * ) Notice: Subject to any disclaimer, the term of this patent is extended or adjusted under 35 U.S.C. 154(b) by 19 days.

(21) Appl. No.: 10/551,655

(22) PCT Filed: Mar. 25, 2004

(86) PCT No.: PCT/JP2004/004214

§ 371 (c)(1),
(2), (4) Date: Jul. 13, 2006

(87) PCT Pub. No.: WO2004/087909

PCT Pub. Date: Oct. 14, 2004

(65) Prior Publication Data

US 2007/0050865 A1 Mar. 1, 2007

(30) Foreign Application Priority Data

Mar. 28, 2003 (JP) ............................. 2003-092337

(51) Int. Cl.
| | |
|---|---|
| C12N 9/88 | (2006.01) |
| C12N 15/00 | (2006.01) |
| C12Q 1/00 | (2006.01) |
| C12Q 1/68 | (2006.01) |
| C12P 21/04 | (2006.01) |
| C07H 21/04 | (2006.01) |

(52) U.S. Cl. ............................. 435/232; 435/4; 435/6; 435/440; 435/69.1; 435/71.1; 536/23.2

(58) Field of Classification Search .................. None
See application file for complete search history.

(56) References Cited

OTHER PUBLICATIONS

Branden et al. Introduction to Protein Structure, Garland Publishing Inc., New York, p. 247, 1991.*
Akashi et al. Molecular and biochemical characterization of 2-hydroxyisoflavanone dehydratas. Involvement of carboxylesterase-like proteins in leguminous isoflavone biosynthesis. Plant Physiol. Mar. 2005;137(3):882-91. Epub Feb. 25, 2005.*
Akashi T. et al., New Scheme of the Biosynthesis of Formononetin Involving 2, 7, 4'-Trihydroxyisoflavanone but Not Daidzein as the Methyl Acceptor., Biosci. Biotechnol. Biochem. (2000), vol. 64, No. 10, pp. 2276 to 2279.
Akashi, T. et al., Cloning and functional expression of a cytochrome P450 cDNA encoding 2-hydroxyisoflavanone synthase involved in biosynthesis of the isoflavonoid skeleton in licorice., Plant. Physiol., (Nov. 1999), vol. 121, No. 3, pp. 821 to 828.

(Continued)

*Primary Examiner*—Yong D Pak
(74) *Attorney, Agent, or Firm*—Young & Thompson

(57) ABSTRACT

2-Hydroxyisoflavanone dehydratase substantially having the amino acid sequence represented by SEQ ID NO: 1 is isolated from licorice. Further, a polynucleotide encoding 2-hydroxyisoflavanone dehydratase of the SEQ ID NO: 2 is obtained. Furthermore, the amino acid sequence of 2-hydroxyisoflavanone dehydratase is identified from soybean and a polynucleotide encoding 2-hydroxyisoflavanone dehydratase is obtained.

3 Claims, 6 Drawing Sheets

OTHER PUBLICATIONS

Akashi, T. et al., cDNA cloning and biochemical charaterization of S-adenosyl-L-methionine: 2,7,4'-trihydroxyisoflavanone 4'-O-methyl transferase, a critical enzyme of the legume isoflavonoid phytoalexin pathway., Plant.Cell Physiol., (Feb. 2003), vol. 44, No. 2, pp. 103 to 112.

Hamanatsuka, T. et al., Purification of 2-hydroxyisoflavonone dehydratase from the cell cultures of *Pueraria labata.*, Phytochemistry (1998), vol. 49, No. 2, pp. 497 to 505.

* cited by examiner

POLYNUCLEOTIDE ENCODING 2-HYDROXYISOFLAVANONE DEHYDRATASE AND APPLICATION OF THE SAME

TECHNICAL FIELD

The present invention relates to a 2-hydroxyisoflavanone dehydratase that catalyzes a dehydration reaction of 2-hydroxy hisoflavanone, novel polynucleotides encoding it, and uses thereof.

BACKGROUND ART

Isoflavones and compounds derived therefrom (i.e., isoflavonoids) are components unique to leguminous plants and have attracted attention as a health supplement in recent years. In addition, isoflavonoids including isoflavones have been known to play a very important role as antimicrobial agents and symbiotic signals for the plants to adapt to biological environments.

The simplest skeletal structure of isoflavonoid is isoflavone, which is one of a group of isoflavonoids, produced early by flavanoid metabolism (see FIG. 1). Isoflavones and their glycosides are accumulated in organs of leguminous plants. Daidzein (7,4'-dihydroxyisoflavone) and genistein (5,7,4'-trihydroxyisoflavone) contained in the free forms and in the form of glycosides in soybean seeds have been known as phytoesterogen (plant esterogen) for the promotion of the health of humans and for the prevention of diseases.

Isoflavone is an intermediate product in the biosynthesis of isoflavonoids having ecophysiological activity, such as antimicrobial phytoalexins having a pterocarpan or isoflavan skeleton. Approximately 50% of isoflavonoids have functional groups derived from 4'-methoxyl group, and these compounds are mainly derived from 4'-methoxylated isoflavone, formononetin (7-hydroxy-4'-methoxyisoflavone).

The isoflavonoid skeleton is biosynthetically produced from (2S)-flavanone by the action of a cytochrome P450 (P450), i.e., 2-hydroxyisoflavanone synthase (IFS). The IFS catalyzes the hydroxylation of the carbon at position 2 of the flavanoid skeleton with the rearrangement of 1,2-aryl group. The resulting product, 2-hydroxyisoflavanone, is dehydrated to form isoflavone (see FIG. 1).

cDNAs of IFS have been identified in one of the leguminous plants, *Glycyrrhiza echinata* (hereinafter, referred to as "licorice") (Non-Patent Document 1 land Patent Document 1) and soybean (Non-Patent Document 2 and Non-Patent Document 3). In the in vitro assay using recombinant IFS which had been overexpressed in yeast microsomes, a large amount of isoflavone was produced by spontanious dehydration of the initial product, 2-hydroxyisoflavanone, in addition to the initial product (Non-Patent Document land Non-Patent Document 3). Furthermore, it was reported that IFS expressed in insect cells produced only isoflavone (Non-Patent Document 2). In this way, an isoflavone can be produced non-enzymatically from the direct product of IFS reaction. In addition, (2S)-flavanone, the substrate of IFS, is a common component present in both leguminous and non-leguminous plants. Thus, it was expected that a non-leguminous plant containing no isoflavonoids could be transformed to the plant having an ability of producing isoflavones by using the IFS cDNA (Non-Patent Document 4, Non-Patent Document 5, and Non-Patent Document 6).

On the basis of these findings, attempts have been made to produce isoflavone in non-leguminous plants (*Arabidopsis thaliana* and tobacco), which inherently contain no isoflavone, by introduction of a soybean IFS gene. However, the production was as low as around $1/1,000$ of that by soybean seeds (Non-Patent Document 3, Non-Patent Document 7, and Non-Patent Document 8). Therefore, it is considered that IFS alone cannot perform the production of isoflavone in an efficient manner.

On the other hand, the enzymatic activity of 2-hydroxyisoflavanone dehydratase, which converts 2,7,4'-trihydroxyisoflavanone into daidzein, was detected in cells of *Pueraria lobata* (kuzu beans) and the protein thereof was then purified (Non-Patent Document 9 and Non-Patent Document 10). In addition, in experiments conducted by the inventors of the present invention, 2,7-dihydroxy-4'-methoxyisoflavanone was converted into formononetin in licorice cell-free extract but 2,7,4'-trihydroxyisoflavanone was not converted into daidzein (Non-Patent Document 11). These results indicate that the dehydration of 2-hydroxyisoflavanone to isoflavone in plant cells may depend on an enzyme (i.e., 2-hydroxyisoflavaone dehydratase) and the enzyme may have substrate specificity for 2-hydroxyisoflavanones having different substituents.

In this way, the previous studies have revealed that isoflavone cannot be efficiently produced only by IFS and the substrate-specific enzymes play an important role in the dehydration of 2-hydroxyisoflavanones to isoflavones. However, the details of the enzyme (2-hydroxyisoflavanone dehydratase) which contributes to the dehydration of 2-hydroxyisoflavanone, to isoflavones have not been elucidated.

[Patent Document 1]

WO 00/46356 pamphlet

[Non-Patent Document 1]

Akashi, T., Aoki, T. and Ayabe, S. (1999) Cloning and functional expression of a cytochrome P450 cDNA encoding 2-hydroxyisoflavanone synthase involved in biosynthesis of the isoflavonoid skeleton in licorice. Plant Physiol. 121: 821-828.

[Non-Patent Document 2]

Steele, C. L., Gijzen, M., Qutob, D. and Dixon, R. A. (1999) Molecular characterization of the enzyme catalyzing the aryl migration reaction of isoflavonoid biosynthesis in soybean. Arch. Biochem. Biophys. 367: 146-150.

[Non-Patent Document 3]

Jung, W., Yu, O., Lau, S. M., O'Keefe, D. P., Odell, J., Fader, G. and McGonigle, B. (2000) Identification and expression of isoflavone synthase, the key enzyme for biosynthesis of isoflavones in legumes. Nature Biotechnol. 18: 208-212.

[Non-Patent Document 4]

Dixon, R. A. and Steele, C. L. (1999) Flavonoids and isoflavonoids—a gold mine for metabolic engineering. Trends Plant Sci. 4: 394-400.

[Non-Patent Document 5]

Humphreys, J. M. and Chapple, C. (2000) Molecular 'pharming' with plant P450s. Trends Plant Sci. 5: 271-272.

[Non-Patent Document 6]

Feldmann, K. A. (2001) Cytochrome P450s as genes for crop improvement. Curr. Opin. Plant Biol. 4: 162-167.

[Non-Patent Document 7]

Yu, O., Jung, W., Shi, J., Croes, R. A., Fader, G. M., McGonigle, B. and Odell, J. T. (2000) Production of the isoflavones genistein and daidzein in non-legume dicot and monocot tissues. Plant Physiol. 124: 781-793.

[Non-Patent Document 8]

Liu, C. J., Blount, J. W., Steele, C. L. and Dixon, R. A. (2002) Bottlenecks for metabolic engineering of isoflavone glycoconjugates in *Arabidopsis*. Proc. Natl. Acad. Sci. USA 99: 14578-1458 3.

[Non-Patent Document 9]

Sankawa, U. and Hakamatsuka, T. (1997) Biosynthesis of isoflavone and related compounds in tissue cultures of *Pueraria lobata*. In Dynamic aspects of natural products chemistry. Molecular biological approaches. Edited by Ogura, K. and Sankawa, U. pp. 25-48. Kodansha/Harwood Academic, Tokyo.

[Non-Patent Document 10]

Hakamatsuka, T., Mori, K., Ishida, S., Ebizuka, Y. and Sankawa, U. (1998) Purification of 2-hydroxyisoflavanone dehydratase from the cell cultures of *Pueraria lobata*. Phytochemistry 49: 497-505.

[Non-Patent Document 11]

Akashi, T., Sawada, Y., Aoki, T. and Ayabe, S. (2000) New scheme of the biosynthesis of formononetin involving 2,7,4'-trihydroxyisoflavanone but not daidzein as the methyl acceptor. Biosci. Biotechnol. Biochem. 64:2276-2279.

[Non-Patent Document 12]

Akashi, T., Sawada, Y., Shimada, N., Sakurai, N., Aoki, T. and Ayabe, S. (2003) cDNA cloning and biochemical characterization of S-adenosyl-L-methionine:2,7,4'-trihydroxyisoflavanone 4'-O-methyltransferase, a critical enzyme of the legumes of lavonoid phytoalexin pathway. Plant Cell Physiol. 44:103-112.

[Non-Patent Document 13]

Ayabe, S., Akashi, T. and Aoki, T. (2002) Cloning of cDNAs encoding P450s in the flavonoid/isoflavonoid pathway from elicited leguminous cell cultures. Methods Enzymol. 357: 360-369.

[Non-Patent Document 14]

Nakamura, K., Akashi, T., Aoki, T., Kawaguchi, K. and Ayabe, S. (1999). Induction of isoflavonoid and retrochalcone branches of the flavonoid pathway in cultured *Glycyrrhiza echinata* cells treated with yeast extract. Biosci. Biotechnol. Biochem. 63: 1618-1620.

DISCLOSURE OF THE INVENTION

The present invention is intended to isolate a dehydratase that plays an important role in the process of producing isoflavone in plant cells and to find out the amino acid sequence thereof and a nucleotide sequence encoding the amino acid sequence.

More specifically, the present invention is intended to determine the amino acid structure of 2-hydroxyisoflavanone dehydratase that catalyzes the dehydration of 2-hydroxyisoflavanone to isoflavone and thereby provide a gene encoding the amino acid structure. Furthermore, the present invention is intended to use the gene thus obtained for the production of isoflavonoid including isoflavone.

For solving these problems, at first, the inventors of the present invention have found the presence of a species-specific 2-hydroxyisoflavanone dehydratases through the investigation of the dehydratase activities in both licorice (formononetin-producing plant) and soybean (daidzein-producing plant) extracts. Then, a cDNA that encodes 2,7-dihydroxy-4'-methoxyisoflavanone-2,3-dehydratase (formononetin-synthetic enzyme) was isolated from licorice by the use of an advanced gene-cloning method named "Function expression Fractionation Screening" (Non-Patent Document No. 12). Furthermore, using the sequence information obtained as above, another cDNA of an analogous enzyme having a different substrate specificity, i.e., 2,7,4'-trihydroxyisoflavanone-2,3-dehydratase (daidzein-synthesizing enzyme) of soybean was obtained.

The novel gene that encodes 2-hydroxyisoflavanone dehydratase may allow for the increasing production of isoflavonoid in a non-leguminous plant by introduction of the gene in the plant.

In addition, it was confirmed that isoflavonoids can be produced using a microorganism cotransformed with the gene encoding 2-hydroxyisoflavanone dehydratase and the gene encoding IFS.

Furthermore, the inventors of the present invention have found that the amino acid sequence of 2-hydroxyisoflavanone dehydratase contains a motif which is known to be present in carboxylesterases. These findings suggest that analogous proteins may be widely distributed over higher plants and a part of dehydration in the biosynthesis of natural products may be mediated by this enzyme family.

Consequently, the present invention pertains to 2-hydroxyisoflavanone dehydratase contained in licorice, particularly to 2,7-dihydroxy-4'-methoxyisoflavanone-2,3-dehydratase (formononetin synthetic enzyme) and a nucleotide sequence encoding the same.

The 2-hydroxyisoflavanone dehydratase contained in licorice comprises a sequence of amino acids 1-328 which is represented by SEQ ID NO: 1. A cDNA sequence encoding the 2-hydroxyisoflavanone dehydratase is represented by SEQ ID NO: 2. Furthermore, the present invention also pertains to a recombinant DNA that expresses the novel gene and a transformant into which the gene is incorporated. The transformant is preferably yeast or *Escherichia coli*. The strain K12 of *E. coli* which is transfected with the gene is deposited as the Accession No. FERM P-19257 (Date of deposition: Mar. 20, 2003) at the International Patent Organism Depositary, National Institute of Advanced Industrial Science and Technology, Tsukuba Central 6, 1-1 Higashi, Tsukuba, Ibaraki, Japan, followed by being transferred to the international deposition under the Budapest Treaty on Mar. 15, 2004 as the Accession No. FERM BP-08662.

Furthermore, the present invention pertains to a method of producing isoflavonoids including isoflavones by a microorganism such as yeast, *E. coli* or a plant into which the gene is incorporated with or without a gene encoding IFS. The yeast preferably used for transformation is *Saccharomyces cerevisiae* strain BJ2168 (Nippon Gene Co., Ltd.). Besides, vectors for yeast transformation include pYES2 (Invitrogen Corporation), pESC-LEU (Stratagene), pESC-TRP (Stratagene), and pESC-HIS (Stratagene), etc.

The present invention also pertains to one of 2-hydroxyisoflavanone dehydratases in soybean, 2,7,4'-trihydroxyisoflavanone dehydratase (daidzein synthetic enzyme) and a nucleotide sequence encoding the same. The 2-hydroxyisoflavanone dehydratase in soybean is analogous to the 2-hydroxyisoflavanone dehydratase in licorice. However, the dehydratase in licorice uses a 4'-methoxyisoflavanone as a substrate, while the dehydratase in soybean uses a 4'-hydroxy isoflavanone as a substrate, and comprises a sequence of amino acids 1-319 represented by SEQ ID NO: 3. A cDNA sequence encoding the 2-hydroxyisoflavanone dehydratase in soybean is represented by SEQ ID NO: 4. Furthermore, the present invention also pertains to a recombinant DNA that expresses the novel gene and a transformant into which the gene is incorporated. The transformant is preferably yeast or *Escherichia coli*. The strain K12 of *E. coli* which is transfected with the gene is deposited as the Accession No. FERM P-19256 (Date of deposition: Mar. 20, 2003) at the International Patent Organism Depositary, National Institute of Advanced Industrial Science and Technology, Tsukuba Central 6, 1-1 Higashi, Tsukuba, Ibaraki, Japan, followed by being transferred to the international deposition under the Budapest Treaty on Mar. 15, 2004 as the Accession No. FERM BP-08661.

Furthermore, the present invention pertains to a method of producing isoflavonoids including isoflavones by a microorganism such as yeast, *E. coli* or a plant into which the gene is incorporated with or without a gene encoding IFS. The yeast preferably used for transformation is *Saccharomyces cerevisiae* strain BJ2168 (Nippon Gene Co., Ltd.). Besides, vectors for yeast transformation include pYES2 (Invitrogen Corporation), pESC-LEU (Stratagene), PESC-TRP (Stratagene), and pESC-HIS (Stratagene), etc. The yeast *Saccharomyces cerevisiae* strain BJ2168, into which the gene of interest and the IFS-encoding gene are coincorporated, is deposited as the Accession No. FERM BP-08663 (Date of deposition: Mar. 15, 2004) at the International Patent Organism Depositary, National Institute of Advanced Industrial Science and Technology, Tsukuba Central 6, 1-1 Higashi, Tsukuba, Ibaraki, Japan.

BEST MODE FOR CARRYING OUT THE INVENTION

Figure 1:
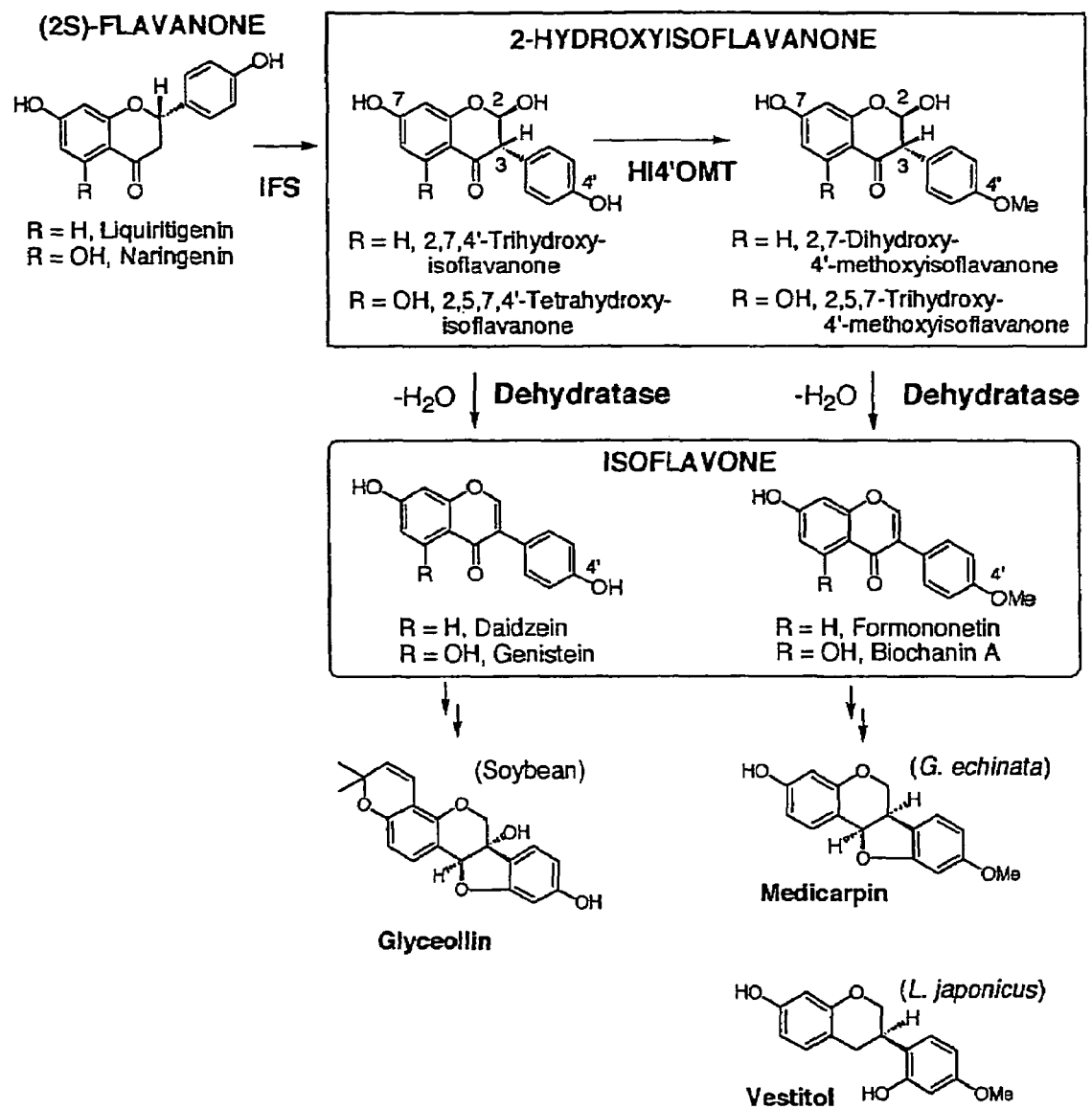
FIG. 1 is a diagram illustrating the production pathway from flavanone to isoflavonoids.

Hereinafter, the present invention will be described concretely.

In the present specification, the 2-hydroxyisoflavanone dehydratase protein of licorice may be referred to as "HIDM", the gene encoding the protein may be referred to as "HIDM", the 2-hydroxyisoflavanone dehydratase protein of soybean may be referred to as "HIDH", and the gene encoding the protein may be referred to as "HIDH".

The present invention pertains to 2-hydroxyisoflavanone dehydratase substantially having an amino acid sequence represented by SEQ ID NO: 1 or 3. As used herein, the phrase "which substantially has the amino acid sequence" means that the amino acid sequence includes ones having any amino acid mutation such as deletion, substitution, addition, and/or insertion as far as the amino acid sequence defines the activity of 2-hydroxyisoflavanone dehydratase. The number of amino acids to be involved in the deletion, substitution, addition, or insertion may be, for example, 1 to 20, preferably 1 to 10, and particularly 1 to 5. Particularly contemplated is, the amino acid sequence in which an amino acid residue is substituted with an amino acid having similar characteristics. The typical substitution occurs: among Ala, Val, Leu, and Ile; between Ser and Thr; between Asp and Glu; between Asn and Gln; between Lys and Arg; and between Phe and Tyr.

Furthermore, the present invention pertains to a polynucleotide substantially having the nucleotide sequence represented by SEQ ID NO: 2 or 4, or a nucleotide sequence complementary to the nucleotide sequence. In the present invention, the phrase "substantially having the nucleotide sequence" means that the nucleotide sequence includes a nucleotide sequence encoding 2-hydroxyisoflavanone dehydratase, and a nucleotide sequence having a difference from the sequence due to the nucleotide degeneracy and having an appropriate additional sequences on the 5'-end, 3'-end, or both ends.

EXAMPLES

Hereinafter, the present invention will be concretely described with reference to the following examples. However, the present invention is not limited to the examples.

<Materials and Methods>

Materials and methods used in the present invention are as follows.

(1) Chemical Materials

Daidzein, genistein, and biochanin A were obtained from Extrasynthese Co., Ltd., and (RS)-narigenin and p-nitrophenyl butyrate were obtained from Sigma Corporation. Formononetin was obtained from a stock in the inventors' laboratory.

Both 2,7,4'-trihydroxyisoflavanone (Non-Patent Document 13) and 2,7-dihydroxy-4'-methoxyisoflavanone (Non-Patent Document 12) were prepared as follows.

The 2,7,4'-trihydroxyisoflavanone was prepared by incubating a yeast microsome expressing CYP93C2 (IFS), liquiritigenin and NADPH, extracting with ethyl acetate, and separating by silica-gel TLC, followed by purification with reverse-phase HPLC. The 2,7-dihydroxy-4'-methoxyisoflavanone was prepared by extracting a reaction mixture of S-adenosyl-L-methionine (SAM), 2,7,4'-trihydroxyisoflavanone, and recombinant 2,7,4'-trihydroxyisoflavanone 4'-O-methyl transferase (HI4'OMT) with ethyl acetate and then separating with silica gel TLC, followed by purification with HPLC.

2,5,7,4'-Tetrahydroxyisoflavanone was prepared by incubating yeast microsome expressing CYP93C2 (Non-Patent Document 1), (RS)-narigenin, and NADPH. The resulting product ($R_f$ 0.30) was purified with silica gel thin-layer chromatography (TLC) [Kieselgel F254 (Merck Ltd.); solvent=toluene:ethyl acetate:methanol:petroleum ether=6:4:1:3].

(2) Plant Materials

Licorice cultured cells (strain AK-1) were established from the leaf and leaf stalk of *Glycyrrhiza echinata* in accordance with the document (Non-Patent Document 1). In a 1/2-concentrated Murashige-Skoog culture medium (solidified with 0.3% (w/v) gellan gum) containing α-napthalene acetic acid (1 μg/ml) and N6-benzyl adenine (1 μg/ml), the cells were cultured under 12-hour photoirradiation (6,000 luxes) and 12-hour darkness in cycles and then treated with elicitor to establish a cDNA library. The suspended culture was kept in the Murashige-Skoog culture medium supplemented with 2,4-dichlorophenoxyacetic acid (0.1 μg/ml) and kinetin (0.1 μg/ml) in dark place. The elicitor treatment was carried out using a yeast extract (Invitrogen Corporation) at a concentration of 0.2% (w/v medium) (Non-Patent Document 14).

Seeds of soybean (*Glycine max* L.CV. Mikawashima: Tohoku Ltd.) were immersed in water for 24 hours and then seeded on a filter paper placed in a conical beaker. The soybean raised from seeds was grown for one week at room temperature under the conditions of 12-hour brightness and 12-hour darkness in cycles.

(3) Preparation of Cell-free Extract

All procedures were carried out at 4° C. Licorice cells (10 g) after elicitor treatment (for 24 hours) or 1-week old soybean raised from seeds (10 g) were homogenized in a mortar with 10 ml of a 100-mM potassium phosphate buffer (pH 7.5) containing 10% sucrose and 14 mM of 2-mercaptoethanol and with sea sand (2.5 g). The resulting homogenate was filtered through gauze and then centrifuged at 10,000×g for 10 minutes. Supernatant was mixed with 2.5 g of Dowex 1-X2 (equilibrated with a 100-mM potassium phosphate buffer), followed by standing for 20 minutes. The solution obtained from the filtration was fractionated with ammonium sulfate and a 30-80% saturated fraction was then demineralized through a Sephadex G-25 column and dissolved in a 100-mM potassium phosphate buffer (pH 7.5) containing 10% sucrose and 14-mM 2-mercaptoethanol, followed by being used in the assay (approximately 600 μg/ml of protein).

(4) Assay of 2-hydroxyisoflavanone Dehydratase

An enzyme preparation was added to 2,7,4'-trihydroxyisoflavanone, 2,7-dihydroxy-4'-methoxyisoflavanone, or 2,5,7,4'-tetrahydroxyisoflavanone (5 nmol each) in 2-methoxyethanol so as to be in a total volume of 100 μl, and then the whole was incubated at 30° C. for 10 minutes.

The assay of 2,5,7-trihydroxy-4'-methoxyisoflavanone dehyderatase (biochanin A synthetase) was carried out as follows. 2,5,7,4'-tetrahydroxyisoflavanone (10 nmol) dissolved in 2-methoxyethanol was incubated together with licorice HI4'OMT (1 μg) and 1 μmol of S-adenosyl-L-methionine (SAM) at 30° C. for 15 minutes.

A concentrated ethyl acetate extract was incubated with recombinant licorice HIDM (1 μg) at 30° C. for 10 minutes. An ethyl acetate extract from the mixture was analyzed by high-performance liquid chromatography (HPLC). The HPLC for both daidzein and formononetin analysis was carried out using a Capcell pak C18 MG column (4.6×150 mm; Shiseido Co., Ltd.) at 40° C. (flow volume=0.8 ml/min) (Non-Patent Document 12) with a linear gradient elution for 40 minutes from 35% to 55% methanol in 3% aqueous acetic acid. 5-Hydroxyisoflavones were analyzed using a Capcell pak C18MG column (4.6×150 mm; Shiseido Co., Ltd.) with a 50% methanol aqueous solution (for genistein) or a 55% methanol aqueous solution (for biochanin A) at 40° C. (flow rate=0.8 ml/min).

The purified recombinant protein (approximately 10 ng of protein) and cell-free extracts of licorice and soybean (approximately 10 μg of protein) were used to determine their specific activity. The concentration of isoflavone was calculated from the HPL peak area of the standard sample of each of daidzein, formononetin, and genistein.

(5) Cloning of cDNA (HIDM) Encoding 2,7-dihydroxy-4'-methoxyisoflavanone dehydratase of licorice cells The expression of protein and the preparation of a crude extract of *E. coli* were carried out as described in a previous document (Non-Patent Document 12).

A cDNA expression library constructed from licorice cells subjected to an elicitor treatment with a yeast extract (6 or 12 hours) (Non-Patent Document 12) was used for screening.

The licorice λZapII cDNA library was converted into a phagemid from by in vivo excion using Exassist helper phage (Stratagene Corporation) and *E. coli* DH5α a F' IQ (Invitrogen Corporation).

Phagemid was introduced into DH5α F' IQ and then *E. coli* cells proliferated on an agar plate with Luria-Bertani (LB)/ampicillin (50 μg/ml). From a mother plate, five independent cDNA fraction pools were prepared, each of which contained approximately 30,000 *E. coli* transformants in LB/ampicillicin (50 μg/ml) culture medium. Subsequently, the cells were incubated in a LB-liquid medium containing 5 mM of IPTG and then collected, followed by preparing a crude enzyme solution.

Figure 2:
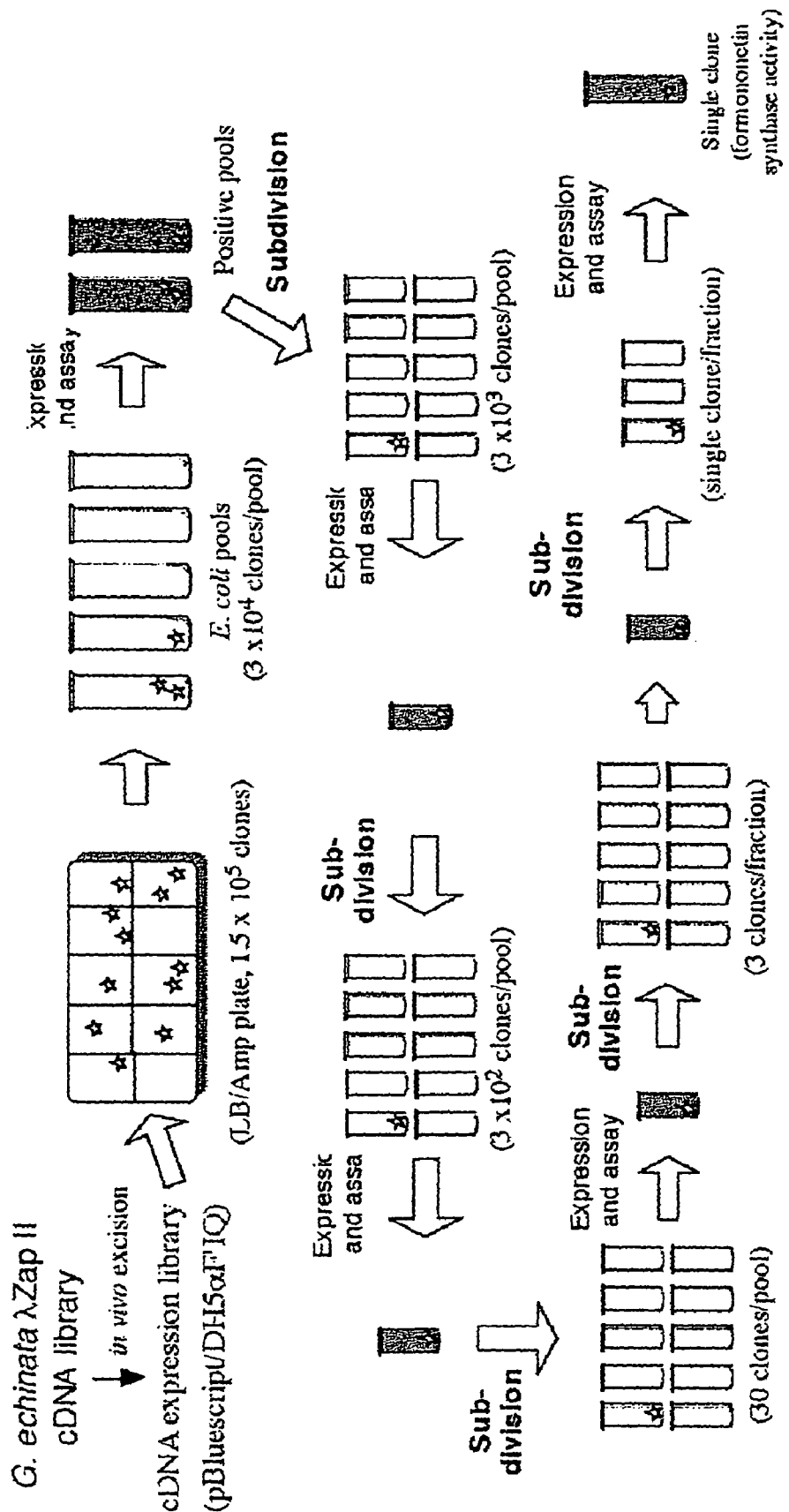
FIG. 2 is a diagram illustrating the cloning of cDNA that encodes 2-hydroxyisoflavanone dehydratase in licorice cells.

Recombinant licorice HI4'OMT (50 ng) was added to 2,7,4'-trihydroxyisoflavanone (0.4 nmol) dissolved in 2 μl of 2-methoxyethanol (Non-Patent Document 12) and then pre-incubated in the presence of 0.4 nmol of S-adenosyl-L-[methyl-$^{14}$C] methionine ([$^{14}$C] SAM, 2.26 GBq/mmol, Amersham Biosciences Corporation) at 30° C. for 3 minutes (total volume=50 μl). Subsequently, the crude extract of *E. coli* pool (100 μl) was added to the mixture and then the whole was further incubated at 30° C. for 10 minutes. The reaction was terminated by the addition of ethyl acetate, the ethyl acetate extract of the mixture was developed through silica gel TLC [LK6DF (Whatman Ltd.); solvent used was chloroform:acetone:25% ammonium solution=70:29:1; 2,7-dihydroxy-4'-methoxyisoflavanone ($R_f$ 0.15), formononetin ($R_f$ 0.30)], and then analyzed by an image analyzer (Typhoon 8600, Amersham Biosciences Corporation). A positive pool, which generated [$^{14}$C] formononetin, was selected for a subsequent screening and divided into ten small-sized pools (approximately 3,000 clones/pool). The fractionation of the positive pool and assay were repeated four times to isolate a clone (HIDM) showing 2,7-dihydroxy-4'-methoxyisoflavanone dehydratase activity (see FIG. 2).

The plasmid was collected, and a nucleotide sequence was then determined using an auto-sequencer (LIC-4000, Aloka Co., Ltd.).

(6) Cloning of Soybean cDNA Homologous to HIDM

Poly (A)+ RNA was isolated from soybean raised from seeds using RNeasy Plant Mini Kit (Qiagen Ltd.) and cDNA was then synthesized using Ready-To-Go T-Primed First Strand Kit (Amersham Biosciences Corporation).

Two PCR-specific primers containing a NdeI or BamHI site (underlined part) were designed from a coding region of TC98460 of soybean EST, which designated initiation and termination codon sequences (TC98-Fow, GT CATATGGCGAAGGAGATAGTGAA (SEQ ID NO: 5); TC98-Rev, AGGGATCCATCAAACCAGAAAAGA (SEQ ID NO: 6)). The cDNA (HIDH) obtained by the reverse transcription (RT)-PCR with these primers using soybean cDNA as template was cloned into a pT7Blue T-vector (Novagen Ltd.) to determine its nucleotide sequence.

(7) Heterologous Expression of Licorice HIDM and Soybean HIDH in E. coli

Two primers containing a NdeI or BamHI site (underlined part) were designed from a coding region of the licorice HIDM (GeDchy-F, GT CATATGGCTTCTTCAACCTCAAC (SEQ ID NO: 7) GeDehy-R, CTGGATCCTCAAACAAGGAAGGAAG (SEQ ID NO: 8)).

The NdeI-BamHI fragment of the PCR product from licorice HIDM was cloned into the corresponding sites of pET28a (Novagen Ltd.). In addition, the NdeI-BamHI fragment of soybean cDNA (HIDH) was also subcloned into the corresponding sites of the pET28a. The expression and purification of recombinant 2-hydroxyisoflavanone dehydratases were carried out by the following procedures (Non-Patent Document 12). The E. coli BL21 (DE3) cells transformed with the vector containing HIDM or HIDH were incubated up to OD600=0.4 in a LB/ampicillin medium supplemented with 20 ml of 50 µg/ml kanamycin or ampicillin at 30° C. IPTG was added to the culture so as to be a final concentration of 1.0 mM and the whole was incubated at 30° C. for six hours. The licorice HIDM and soybean HIDH were purified from the crude extracts of HIDM and HIDH-expression E. coli using HisTrap Kit (Amersham Biosciences Corporation), respectively.

(8) Preparation of Recombinant Yeast by which 2-hydroxyisoflavanone Synthase (IFS) and 2-hydroxyisoflavanone Dehydratase are Co-expressed Vector (pYES-CYP93C2) used for the expression of IFS (CYP93C2) of licorice in yeast was those described in Non-Patent Document 1 and Patent Document 1 (the coding region of the CYP93C2 gene was cloned into the KpnI and EcoRI sites downstream of a galactose induction promoter GAL1 of a yeast expression vector (pYES2, Invitrogen Corporation)).

The vector (pESC-HIDE) for the expression of soybean 2-hydroxyisoflavanone dehydratase (HIDH) was prepared as follows. Two different primers added with ApaI and XhoI sites (underlined portions) [HIDH-F1 (5'-G GGGCCCGGATCCATGGCGAAGGAGATAGTGAAAG-3' (SEQ ID NO: 9)) and HIDH-R1 (5'-GG GAGCTCGAGTCAAACCAGAAAAGAAGCC-3' (SEQ ID NO: 10)] were designed from the coding region of soybean 2-hydroxyisoflavanone dehydratase (HIDH).

The primers and KOD polymerase (Toyobo Co., Ltd.), as well as soybean HIDH cDNA as a template, were subjected to a PCR (98° C. for 15 sec, 60° C. for 15 sec, and 74° C. for 30 sec in 15 cycles).

The PCR product was treated with ApaI and XhoI and then inserted into ApaI and XhoI sites downstream of galactose induction promoter GAL1 of an yeast expression vector (pESC-Leu, Stratagene) to produce pESC-HIDE.

The yeast, Saccharomyces cerevisiae strain BJ2168 (a; prc1-3407, prb1-1122, pep-4-3, leu2, trp1, ura3-511) (Nippon Gene Co., Ltd.), was transformed using an electroporation device (Cellject Duo, Thermo Electron Corporation). The electropolaration was carried out according to the procedures recommended by Thermo Electron Corporation. The transformants were selected in a culture medium containing a yeast nitrogen base without amino acids (6.7 g/l, Invitrogen Corporation), glucose (20 g/l), tryptophan (20 mg/i), and agar (20 g/l). The following three recombinant yeasts were prepared: (1) control yeast (pYES2 and pESC-Leu were introduced into strain BJ2168), (2) IFS expression yeast (pYES-CYP93C2 and pESC-Leu were introduced into strain BJ2168), and (3) IFS and 2-hydroxyisoflavanone dehydratase co-expression yeast (pYES-CYP93C2 and pESC-HIDH were introduced into strain BJ2168).

(9) Determination of Carboxylesterase Activity

The specific carboxylesterase activities of recombinant licorice HIDM and soybean HIDH proteins were calculated from the generation rate of p-nitrophenol measured at 30° C. by an absorbance at 400 nm in 1.5 ml of a 50-mM Tris-HCl buffer containing 150 mM of NaCl and 750 nmol of p-nitrophenyl butyrate (Heymann 1981). Commercially-available pig liver carboxylesterase (Sigma Corporation) was used as a positive control. Thermally-denatured (100° C., 10 minutes) licorice HIDM, soybean HIDH, and pig liver carboxylesterase protein were analyzed as negative controls, respectively.

(10) RT-PCR Analysis

Suspension-cultured licorice cells were treated with yeast extract (Invitrogen Corporation) and then harvested at time periods of 3, 6, 12, 24, and 48 hours after treatment (Non-Patent Document 1). In addition, mRNA was extracted using a Straight A's mRNA isolation system (Novagen Ltd.) to synthesize cDNA. For the RT-PCR, specific primers designed from licorice HIDM, IFS (Non-Patent Document 12) and HI4'OMT (Non-Patent Document 12) were used. The reaction was initiated by denaturation at 94° C. for one minute and then three incubation steps (94° C. for 1 min; 55° C. for 1 min; and 72° C. for 1 min) were repeated for 30 cycles. The product was subjected to 1.2% (w/v) agarose gel electophoresis and then stained with ethidium bromide.

The results of the present invention obtained by the above materials and methods will be described below.

(1) 2-hydroxyisoflavanone Dehydratase Activities in Licorice Cells and Soybean Raised from Seeds After the elicitor treatment, the licorice cells accumulate medicarpin (a 4'-methoxyisoflavonoid, see FIG. 1) but not 4'-hydroxyisoflavonoids (Nakamura et al. 1999). Soybeans are known to produce glycoconjugates of 4'-hydroxylated isoflavones, daidzein, genistein and glycitein (Dewick 1986, Dewick 1993, and Aussenac 1998). Therefore, it seems that the extracts from licorice cells and soybean raised from seeds have activities to produce formononetin and daidzein from 2-hydroxyisoflavonones with appropriate substitutions, respectively. The results obtained by investigating those activities using HPLC are shown in Table 1.

TABLE 1

Specific activities of 2-hydroxyisoflavanone dehydratase and carboxylesterase in the crude extracts and recombinant proteins of licorice and soybean

| | | Specific activity (a), (b) | | | | |
|---|---|---|---|---|---|---|
| | | Licorice | | Soybean | | |
| Substrate | Product | Crude extract (c) (pkatal/mg) | Recombinant protein (d) (nkatal/mg) | Crude extract (c) (pkatal/mg) | Recombinant protein (d) (nkatal/mg) | Carboxylesterase from pig liver (nkatal/mg) |
| 2,7-dihydroxy-4'-methoxyisoflavanone | formononetin | 123.0 ± 8 | 52.1 ± 1.5 | 97.4 ± 10 | 0.90 ± 0.1 | — (e) |
| 2,5,7,4'-tetrahydroxyisoflavanone | genistein | — (e) | — (e) | 19.6 ± 3 | 3.55 ± 0.6 | — (e) |
| 2,7,4'-trihydroxyisoflavanone | daidzein | 0.8 ± 0.03 | 0.70 ± 0.08 | 197.3 ± 15 | 43.6 ± 4 | 0 |
| p-nitrophenyl butyrate | p-nitrophenol | — (e) | 0.32 ± 0.07 (f) | — (e) | 7.20 ± 0.4 (f) | 425 ± 7 (f) |

(a) Mean ± SD from three independent experiments.
(b) Specific activities were calculated from the rate of isoflavone and p-nitrophenol production.
(c) Ammonium sulfate (30% to 80% saturation) precipitate of the cell-free extract of licorice cells (strain AK-1) elicited with 0.2% yeast extract for 24 hours or the cell-free extract of soybean seedling.
(d) Purified recombinant proteins were used for the assays.
(e) Unanalyzed.
(f) No hydrolyzing activity was detected in assays with heat-treated (100° C., 10 minutes) proteins and p-nitrophenyl butyrate.

As is evident from Table 1, when 2,7-dihydroxy-4'-methoxyisoflavanone was incubated with the cell-free extract of licorice, formononetin was produced. A small amount of daidzein produced from 2,7,4'-trihydroxyisoflavanone with the licorice extract was observed but the activity thereof was approximately 160 times as small as the production of formononetin.

In the case of the cell-free extract from soybean raised from seeds, it was detected that formononetin and daidzein were produced at a ratio of roughly 1:2 from 2,7-dihydroxy-4'-methoxyisoflavanone (from which formononetin is produced) and 2,7,4'-trihydroxyisofravonone (from which daidzein is produced). Furthermore, the soybean extract catalyzed the production of genistein from 2,5,7,4'-tetrahydroxyisoflavanone at a level of approximately 1/10 with respect to the production of daidzein.

On the other hand, spontaneous dehydration of 2-hydroxyisoflavanone could be ignored under experimental conditions in which the concentration of a substrate was 50 μM in a neutral buffer (pH 7.5). These results strongly suggest that the dehydration of 2-hydroxyisoflavanone which forms isoflavone in plant cells is an enzyme-catalyzed reaction. Furthermore, it seems that licorice and soybean have different substrate specificities with respect to 2-hydroxyisoflavanone dehydratase.

(2) The Preparation of 2-hydroxyisoflavanone Dehydratase cDNA of Licorice by Functional Expression Fractionation Screening.

The high sensitive and the specific detection of the conversion from 2,7-dihydroxy-4'-methoxyisoflavanone to formononetin was made possible using the purified 2,7,4'-trihydroxyisoflavanone prepared by recombinant IFS in yeast (Non-Patent Document 1), [$^{14}$C]-SAM, and affinity-purified recombinant licorice HI4'OMT having 6 histidine residues at the N-terminus (Non-Patent Document 12) to produce [$^{14}$C]-2,7-dihydroxy-4'-methoxyisoflavanone prior to the assay. The screening of cDNA of the dehydratase was carried out using a cDNA expression library prepared from licorice cells treated with yeast extract (Non-Patent Document 12). The initial screening was performed on five cDNA pools (30,000 transformants/pool). The extract from the E. coli pool was analyzed such that it was allowed to react with the above mixture which produced [$^{14}$C]-2,7-dihydroxy-4'-methoxyisoflavanone and then an ethyl acetate extract from the reaction mixture was analyzed by TLC autoradiography. It was found that two pools produced [$^{14}$C] formononetin. One of the positive pools optionally chosen was fractionated into ten small-sized pools (approximately 3,000 clones/pool). The expression and analysis of protein were carried out again, and a positive pool was then identified from 10 pools. The positive pool was repeatedly fractionated and analyzed. One positive pool out of the 10 pools was repeatedly identified from third (approximately 300 clones/pool), fourth (30 clones/pool), and fifth (3 clones/pool) screenings. Finally, a single E. coli clone representing 2,7-dihydroxy-4'-methoxyisoflavanone dehydratase activity was isolated (see FIG. 2).

Figure 3:
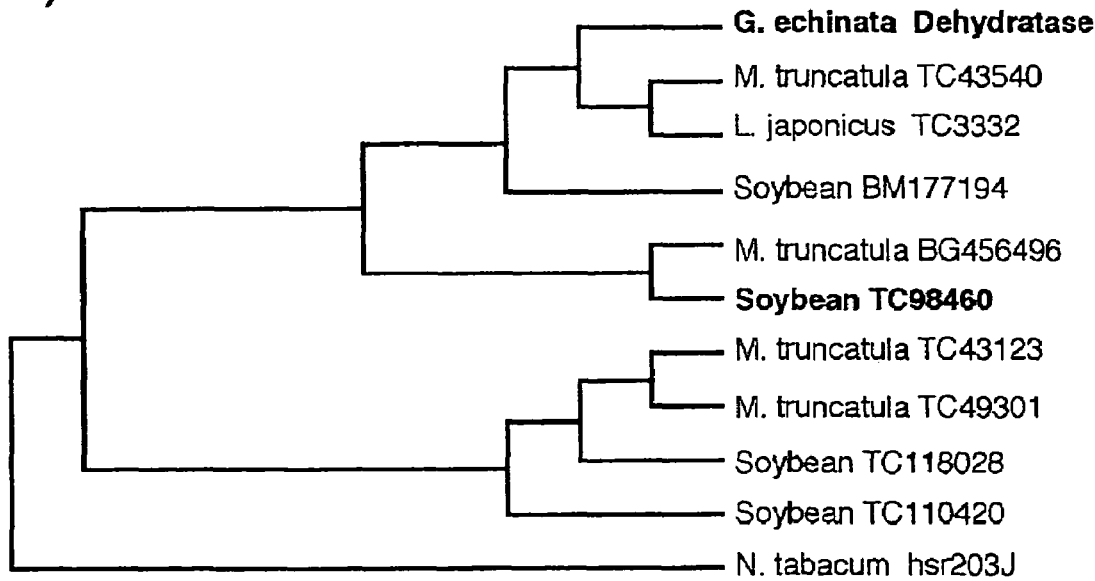
FIG. 3A shows the amino acid sequences of 2-hydroxyisoflavanone dehydratases in licorice and soybean (top sequence corresponds to 2-hydroxyisoflavanone dehydratase (licorice) represented by SEQ ID NO: 1; bottom sequence corresponds to 2-hydroxyisoflavanone dehydratase (soybean) represented by SEQ ID NO: 3).
FIG. 3B shows a molecular phylogenetical tree for the genes of leguminous plants, including licorice (*G. echinata* Dehydratase=licorice HIDM, Soybean TC98460=soybean HIDH).

The cDNA encoding the enzyme was collected, and then the sequence was determinated sequence using a sequencer. The cDNA of HIDM (2-hydroxyisoflavanone dehydratase methoxy type) has a 1,178-bp nucleotide and encoded 328 amino acids (FIG. 3A). The search for protein-protein BLAST revealed that an estimated amino acid sequence of licorice HIDM indicates 40% identity with putative proteins of Arabidopsis thaliana (Accession NOS: Atlg47480, AT3g48690, and At3g48690), 34% identity with Nicotiana tabacum hsr203J (Accession NO: X77136) (Pontier et al., 1994), 31% identity with pea E86 (Accession NO: AB026296) (Ichinose et al., 2001), and 32% identity with carboxylesterase of Archaeoglobus fulgidus (thermophilic sulfur bacteria) (Accession NO: 1JJIA) (Manco et al., 2000). In addition, the licorice HIDM had the motif of a conserved sequence recorded for carboxylesterases (approximately 40 to 180 amino acids from the N-terminal).

Conserved sequences (His85-Gly86-Gly87, a boxed sequence in FIG. 3A) shared with lipases and esterases to form an oxy anion hole were present in the motif of carboxylesterase (Contreras et al., 1996, Laurell et al., 2000, and Hosokawa 2000). In the licorice HIDM protein, even though the Ser residue stored in catalytic triads in typical lipase and esterase (Osterlund et al., 1996, Contreras et al., 1996, Manco et al., 2000, and Hosokawa 2002) was substituted by a Thr residue, it was recognized that a hypothetical catalytic triad (Thr 173, Asp 272, and His 304) is found on the outside of the motif of carboxylesterase. In FIG. 3A, the hypothetical catalytic triad (Thr 173, Asp 272, and His 304) is denoted by an asterisk (*)

(3) Search of Homologous cDNA of Licorice Dehydratase in cDNA Libraries of Leguminous Plants By retrieving from the expressed sequence tags (ESTs) of soybean, *Medicago truncatula*, and *Lotus japonicus* (Asamizu et al. 2000), it was revealed that these plants had cDNAs which indicated identity with the licorice HIDM (amino acid identity <50%). However, those sequences have been annotated as hypothetical proteins. A molecular phylogenetical tree represented that soybean BM177194, *L. japonicus* TC3332, and *M. truncatula* TC43540 proteins form the same branch as that of the dehydratase of licorice (amino acid identity <80%) (FIG. 3B) The soybean BG456496 has <60% identity as those of the four proteins, and form the other branch with *M. truncatula* BG456496 (FIG. 3B).

(4) Characterization of Recombinant 2-hydroxyisoflavanone Dehydratases of Licorice and Soybean The EST sequence TC98460 of soybean has predicated initiation and terminal codons. The coding region of cDNA was cloned from soybean seedlings by RT-PCR and designated as HIDH (2-hydroxyisoflavanone dehydratase hydroxy type).

Figure 4:
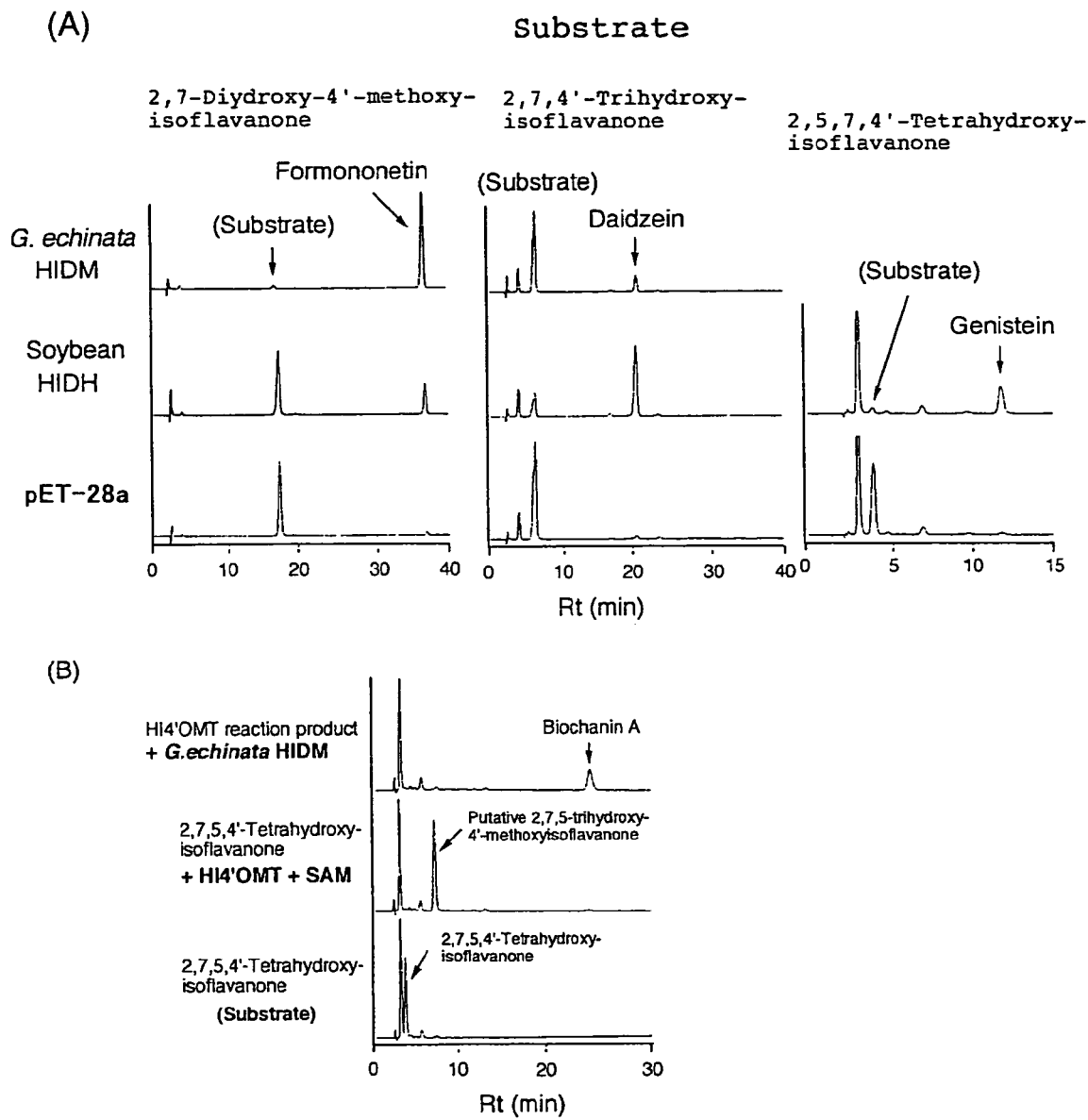
FIG. 4 is a HPLC profile of the product of 2-hydroxyisoflavanone dehydratase.

Licorice HIDM and soybean HIDH were expressed in *E. coli* and recombinant proteins having six histidine residues at the N-terminal were then purified, followed by measuring the activity thereof to 2-hydroxyisoflavanones. As shown in FIG. 4A, the incubation of licorice HIDM with 2,7-dihydroxy-4'-methoxyisoflavanone led to the production of formononetin. The product (formononetin) can be identified and confirmed by making a comparison between the Rt value thereof and the Rt value of a standard sample, as well as carrying out electron impact mass spectrometry (molecular ion peak of m/z 268, and retro-Diels-Alder fragment peak of m/z 132). Furthermore, a small amount of daidzein was produced from 2,7,4'-trihydroxyisoflavanone by licorice HIDM. The specific activity of licorice HIDM to 2,7-dihydroxy-4'-methoxyisoflavanone is 74 times as high as one to 2,7,4'-trihydroxyisoflavanone and shows that the biochemical characteristics of the recombinant protein may correspond to those of a licorice cell-free extract (Table 1).

When the recombinant soybean HIDH was assayed using 2,7,4'-trihydroxyisoflavanone and 2,7-dihydroxy-4'-methoxy isoflavanone, it was confirmed that the respective peaks of daidzein and formononetin emerged on HPLC (FIG. 4A). The chemical structures of isoflavones were reconfirmed by the electron impact mass spectrometry. Furthermore, the soybean HIDH catalyzed the production of genisein from 2,5,7, 4'-trihydroxyisoflavanone (FIG. 4A). As shown in Table 1, the specific activity of HIDH was the highest with respect to 2,7,4'-trihydroxyisoflavanone but comparatively low (approximately 1/10) with respect to another 4'-hydroxylated substrate and extremely low with respect to another substrate having a 4'-methoxy group.

Furthermore, when a compound expected to be 2,5,7-trihydroxy-4'-methoxyisoflavanone, which was obtained by incubating the recombinant licorice HI4'OMT with 2,5,7,4'-tetrahydroxyisoflavanone and SAM, was incubated with the licorice HIDM, biochanin A was detected by HPLC (FIG. 4B).

(5) Carboxylesterase Activity of Recombinant Licorice and Soybean 2-hydroxyisoflavanone Dehydratases In the carboxylesterase assay, p-nitrophenyl butyrate is a substrate commonly used. The recombinant licorice and soybean dehydratases displayed weak activity against p-nitrophenyl butyrate (Table 1). On the other hand, carboxylesterase from pig lever did not dehydrate 2,7,4'-trihydroxyisoflavanone (Table 1).

(6) Gene Expression in Formononetin Pathway in Licorice Cells

Figure 5:
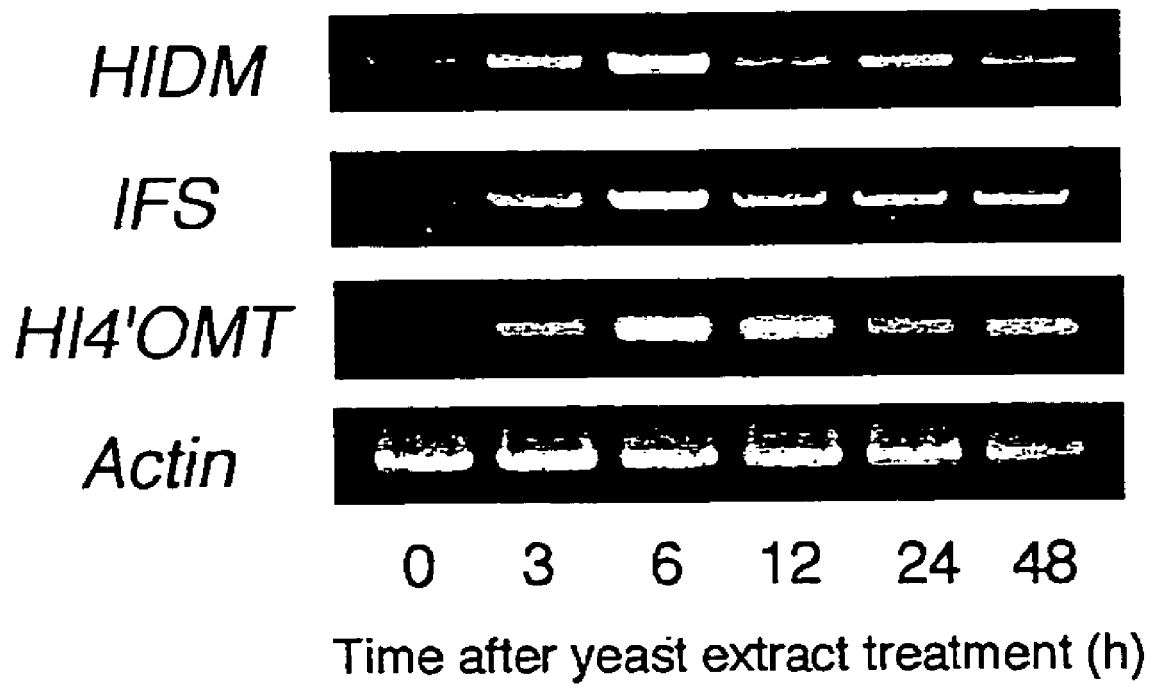
FIG. 5 shows the patterns of RT-PCR analysis, representing the respective gene-expression levels.

The present RT-PCR analysis revealed that transcription levels of HIDM, HI4'OMT, and IFS of licorice cells increased at 6 to 12 hours after the treatment with yeast extracts, respectively (FIG. 5).

(7) Isoflavone Production in Recombinant Yeast where 2-hydroxyisoflavanone Synthase (IFS) and 2-hydroxyisoflavanone Dehydratase were Co-expressed Three different recombinant yeasts were compared with respect to their abilities to produce isoflavone. Here, those yeasts were those described in the previous section for the preparation of recombinant yeast in which 2-hydroxyisoflavanone synthase (IFS) and 2-hydroxyisoflavanone dehydratase of soybean (HIDH) were co-expressed. That is, the yeasts were (1) control yeast (pYES2 and pESC-Leu were introduced into strain BJ2168), (2) IFS expression yeast (pYES-CYP93C2 and pESC-Leu were introduced into strain BJ2168), and (3) IFS and HIDH co-expression yeast (pYES-CYP93C2 and pESC-HIDH were introduced into strain BJ2168).

Each of those three different yeasts was incubated overnight (28° C.) with shaking in a 1.5-ml minimum liquid culture medium [yeast nitrogen base without amino acids (6.7 g/l), glucose (20 g/l), tryptophan (20 mg/l)]. Then, the yeast cells were collected by centrifugation and then the yeast cells were suspended in a 3-ml YPG liquid medium [yeast extract (10 g/l), peptone (20 g/l), galactose (20 g/l)], and incubated overnight to induce protein expression.

Then, the yeast cells were collected by centrifugation and then the yeast cells were suspended in a 0.5-ml YPG liquid medium containing 50 μg of naringenin (dissolved in 5 μl tween 80 and 5 μl ethanol) and then incubated overnight. Glass beads were added to the culture medium to crush the cells, followed by extracting with ethyl acetate. The extract was dried and then dissolved in methanol, followed by analysis on HPLC [column: CAPCELL PAK C18 MG column (4.6×150 mm, Shiseido Co., Ltd.); 40° C.; 0.8 ml/min; solvent, which is linear gradient so as to be 30% methanol (0 min) to 50% methanol (30 min)] Based on a peak area of genistein preparation, the amount of genistein in each sample was obtained.

Figure 6:
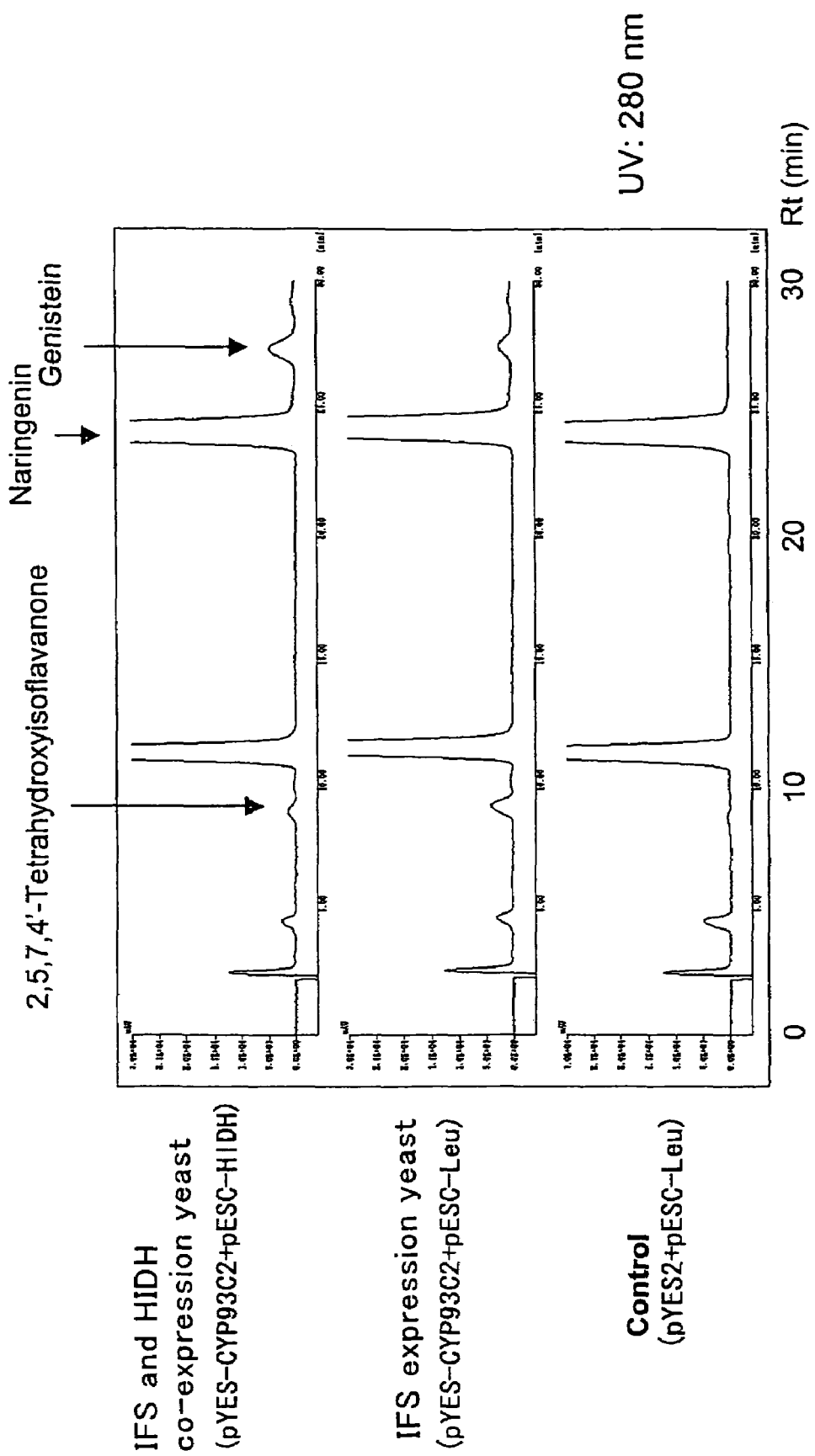
FIG. 6 shows HPLC chromatograms of extracts obtained by incubating the IFS and HIDH co-expression yeast (upper), the IFS expression yeast (middle), and the control yeast (lower) in naringenin-containing media, respectively.

As a result, for each of the recombinant yeast (3) in which IFS and HIDH were co-expressed and the recombinant yeast (2) in which IFS was expressed by itself, the production of genistein and 2,5,7,4'-tetrahydroxyisoflavanone was confirmed on HPLC. For the control yeast (1), the production of either or both compounds could not be observed. The yeast (3) where IFS and HIDH were co-expressed produced 3.2±0.2 μg of genistein (average of three experiments). The recombinant yeast, where IFS was expressed by itself produced 0.8±0.1 μg of genistein (average of three experiments). Thus, it was found that the amount of isoflavone produced increased when IFS and HIDH were co-expressed (see FIG. 6).

From the above results, the followings become evident.

In the present invention, cDNA, which encodes 2-hydroxyisoflavanone dehydratase, licorice HIDM, and soybean HIDH were cloned, respectively.

HIDM and HIDH show different substrate specificity to 2-hydroxyisoflavanone having 4'-methoxyl and 4'-hydroxyl substituents. These enzymes can be referred to as 2,7-dihydroxy-4'-methoxyisoflavanone 2,3-dehydratase (formononetin synthetic enzyme) of licorice and 2,7,4'-trihydroxyisoflavanone 2,3-dehydratase (daidzein synthetic enzyme) of soybean employing the most preferred substrate of each enzyme into the nomenclature. It is important that the substrate specificity can be reflected in the structure of isoflavone contained in each of plant species (and furthermore, isoflavonoid on the downstream of the biosynthetic pathway). Therefore, there is an extremely high probability that the production of isoflavone from 2-hydroxyisoflavanone in plant cells is enzyme-dependent.

The specific activity of 2-hydroxyisoflavanone dehydratase reaction by recombinant licorice HIDM is roughly 400 to 900 times higher than that of the crude extract of licorice. Thus, any of the gene recombinant protein and the crude extract showed an extremely higher selectivity to 2,7-dihydroxy-4'-methoxyisoflavanone than to 2,7,4'-trihydroxy-isoflavanone (see Table 1). It strongly suggests that the main activity of the crude extract may be found in the HIDM protein. Furthermore, as the HIDM mRNA of the induced licorice cells equally accumulate both IFS and HI4' OMT, it is suggested that HIDM may participate in the biosynthesis of formononetin.

On the other hand, the soybean extract catalyzed the dehydration activities against 2,7-dihydroxy-4'-methoxyisoflavanone and 2,7,4'-trihydroxyisoflavanone at a ratio of approximately 1:2. In contrast, the dehydratase activity of recombinant soybean HIDH protein was very specific to a 4'-hydroxylated 2-hydroxyisoflavanone (see Table 1). Consequently, there is a high possibility that HIDH may cause the production of 4'-hydroxylated isoflavone from soybean.

In the present invention, as for a more interesting finding, 2-hydroxyisoflavanone dehydratase is a protein having a sequence which can be classified as carboxylesterase of hydrolase family. Actually, the soybean HIDH had a weak carboxylesterase activity against p-nitrophenyl butyrate (approximately 1/50 of the pig lever enzyme). The present invention has originally demonstrated that the protein in this family may catalyze dehydration.

The characteristic features of 2-hydroxyisoflavanone dehydratase, which was reported with respect to *P. lobata*, correspond to those of the soybean HIDH (Hakamatsuka et al., 1998). The protein of *P. lobata* has a molecular weight of 38 kDa, which approximates a calculated value of the soybean HIDH (35,115). Furthermore, the specific activity (56.8 mkatal/kg protein) of dehydratase of *P. lobata* against 2,7,4'-trihydroxyisoflavanone is almost equal to the activity (43.6 nkatal/mg) of the gene recombinant soybean. Very interestingly, the His residue in the protein of *P. lobata* has been reported very important for the activity of the protein (Hakamatsuka et al., 1998). The His is one of the amino acids in the catalytic triad of carboxylesterase (Satoh and Hosokawa 1995 and Wei et al., 1999). Therefore, 2-hydroxyisoflavanone dehydratase of *P. lobata* may also be a protein in the carboxylesterase family.

Some dehydratase genes/proteins have their own characteristic features which have been determined from several kinds of plants. Those include dehydroquinate dehydratase (Deka et al., 1994), δ-aminolevulinate dehydratase (Kaczor et al., 1994), imidazole glycerol phosphate dehydratase (Tada et al., 1994), and allene oxide synthetic enzyme (Song et al., 1993). However, between those dehydratases and HIDM/HIDH, no significant homology of nucleotide and amino acid sequences can be found.

Proteins having a carboxylesterase motif which is homologous to HIDM/HIDH to some extent are widely distributed to the plant kingdom. In addition, for biosynthetically producing vegetable natural products, there are many dehydration reactions in which the characteristics of enzymes have not been defined. For instance, there is a dehydrative ring-formation of 2'-hydroxyisoflavan-4-ol to form pterocarpan skeleton (Bless and Barz 1988, Guo et al., 1994a, and Guo et al., 1994b). Experiments with the microsome reveals that P450s are responsible for the production of methylene ring and the cyclization of a prenyl substituent on phenol ring during the biosynthesis of isoflavonoids in chickpea and soybean (Clemens and Barz 1996, Welle and Grisebach 1988). However, dehydratase may contribute to those reactions together with P450, and the enzyme protein may be classified in the carboxylesterase family. In addition, it is reported that several plant genes encoding this type of proteins to which no catalytic functions are assigned have been induced in response to pathogenesis (Pontier et al., 1994, Walden et al., 1999, Ichinose et al., 2001, Tronchet et al., 2001, and Benzier et al., 2002). They may be dehydratases which participate in the biosynthesis of defense compounds.

It is very important to identify a 2-hydroxyisoflavanone dehydratase gene for metabolic engineering of leguminous and non-leguminous plants. So far, for the production of isoflavonoid in non-leguminous plants, transgenic *Arabidopsis thaliana* and *Nicotiana tabacum* over expressing soybean IFS have been constructed (Non-Patent Document 3, Non-Patent Document 7, and Non-Patent Document 3). However, the productivity of isoflavonoid in the transformants, was not satisfactory. In a typical case, genistein can be produced approximately 2 to 4 ng per gram fresh weight of *Arabidopsis thaliana* (Non-Patent Document 7, Non-Patent Document 8). On the other hand, isoflavone can be produced approximately 4 to 10 mg per gram dry weight of soybean seeds (Aussenac et al., 1998) and isoflavone can be produced approximately 3 mg per gram fresh weight of lupin seedling (Katagiri et al., 2000). Competition between a metabolic flow from flavanone to 2-hydroxyisoflavanone and another flow to 3-hydroxyflavanone may be a bottle neck for the production of isoflavone intransgenic *Arabidopsis thaliana*, and, indeed, the isoflavone production in *A. thaliana* flavanone 3-hydroxylase mutant transformed with IFS increased to 6- to 31-folds (Liu et al., 2002).

Isoflavone production in a recombinant yeast coexpressing IFS and HIDH were higher that in the recombinant yeast expression IFS. Thus, the amount of isoflavone produced can be expected to increase when IFS and HIDH are coexpressed in non-leguminous plants.

Furthermore, it is feasible to engineer an isoflavonoid pathway of a leguminous plant by genetic engineering using HIDH and HIDM as transgenes.

REFERENCES

Akashi, T., Aoki, T. and Ayabe, S. (1999) Cloning and functional expression of a cytochrome P450 cDNA encoding 2-hydroxyisoflavanone synthase involved in biosynthesis of the isoflavonoid skeleton in licorice. Plant Physiol. 121: 821-828.

Akashi, T., Sawada, Y., Aoki, T. and Ayabe, S. (2000) New scheme of the biosynthesis of formononetin involving 2,7, 4'-trihydroxyisoflavanone but not daidzein as the methyl acceptor. Biosci. Biotechnol. Biochem. 64: 2276-2279.

Akashi, T., Sawada, Y., Shimada, N., Sakurai, N., Aoki, T. and Ayabe, S. (2003) cDNA cloning and biochemical characterization of S-adenosyl-L-methionine: 2,7,4'-trihydroxy-isoflavanone 4'-O-methyltransferase, a critical enzyme of the legume isoflavonoid phytoalexin pathway. Plant Cell Physiol. 44: 103-112.

Aoki, T., Akashi, T. and Ayabe, S. (2000) Flavonoids of leguminous plants: structure, biological activity, and biosynthesis. J. Plant Res. 113: 475-488.

Asamizu, E., Nakamura, Y., Sato, S. and Tabata, S. (2000) Generation of 7137 non-redundant expressed sequence tags from a legume, Lotus japonicus. DNA Res. 7: 127-130.

Aussenac, T., Lacombe, S. and Dayde, J. (1998) Quantification of isoflavones by capillary zone electrophoresis in soybean seeds: effects of variety and environment. Am. J. Clin. Nutr. 68: 1480S-1485S.

Ayabe, S., Akashi, T. and Aoki, T. (2002) Cloning of cDNAs encoding P450s in the flavonoid/isoflavonoid pathway from elicited leguminous cell cultures. Methods Enzymol. 357: 360-369.

Basarab, G. S., Steffens, J. J., Wawrzak, Z., Schwartz, R. S., Lundqvist, T. and Jordan, D. B. (1999) Catalytic mechanism of scytalone dehydratase: site-directed mutagenisis, kinetic isotope effects, and alternate substrates. Biochemistry 38: 6012-6024.

Baudouin, E., Charpenteau, M., Roby, D., Marco, Y., Ranjeva, R. and Ranty, B. (1997) Functional expression of a tobacco gene related to the serine hydrolase family—esterase activity towards short-chain dinitrophenyl acylesters. Eur. J. Biochem. 248: 700-706.

Bezier, A., Lambert, B. and Baillieul, F. (2002) Cloning of a grapevine Botrytis-responsive gene that has homology to the tobacco hypersensitivity-related hsr203J. J. Exp. Bot. 53: 2279-2280.

Bless, W. Barz, W. (1988) Isolation of pterocarpan synthase, the terminal enzyme of pterocarpan phytoalexin biosynthesis in cell suspension cultures of Cicer arietinum. FEBS Lett. 235: 47-50.

Clemens, S. and Barz, W. (1996) Cytochrome P450-dependent methylenedioxy bridge formation in Cicer arietinum. Phytochemistry 41: 457-460.

Contreras, J. A., Karlsson, M., Osterlund, T., Laurell, H., Svensson, A. and Holm, C. (1996) Hormone-sensitive lipase is structurally related to acetylcholinesterase, bile salt-stimulated lipase, and several fungal lipases. Building of a three-dimensional model for the catalytic domain of hormone-sensitive lipase. J. Biol. Chem. 271: 31426-31430.

Deka, R. K., Anton, I. A., Dunbar, B. and Coggins, J. R. (1994) The characterisation of the shikimate pathway enzyme dehydroquinase from Pisum sativum. FEBS Lett. 349: 397-402.

Dewick, P. M. (1986) Isoflavonoids. In The Flavonoids. Advances in Research since 1980, Edited by Harborne, J. B. pp. 125-209, Chapman and Hall, London.

Dewick, P. M. (1993) Isoflavonoids. In The Flavonoids. Advances in Research since 1986 Edited by Harborne, J. B. pp. 117-238, Chapman and Hall, London.

Dixon, R. A. (2002) Genistein. Phytochemistry 60: 205-211.

Dixon, R. A. (1999) Isoflavonoids: biochemistry, molecular biology, and biological functions. In Comprehensive Natural Products Chemistry. Volume 1. Polyketides and other secondary metabolites including fatty acids and their derivatives. Edited by Sankawa, U. pp. 773-823. Elsevier, Amsterdam.

Dixon, R. A. and Steele, C. L. (1999) Flavonoids and isoflavonoids—a gold mine for metabolic engineering. Trends Plant Sci. 4: 394-400.

Feldmann, K. A. (2001) Cytochrome P450s as genes for crop improvement. Curr. Opin. Plant Biol. 4: 162-167.

Guo, L., Dixon, R. A. and Paiva, N. L. (1994a) Conversion of vestitone to medicarpin in alfalfa (Medicago sativa L.) is catalyzed by two independent enzymes. Identification, purification, and characterization of vestitone reductase and 7,2'-dihydroxy-4'-methoxyisoflavanol dehydratase. J. Biol. Chem. 269: 22372-22378.

Guo, L., Dixon, R. A., and Paiva, N. L. (1994b). The 'pterocarpan synthase' of alfalfa: association and co-induction of vestitone reductase and 7,2'-dihydroxy-4'-methoxy-isoflavanol (DMI) dehydratase, the two final enzymes in medicarpin biosynthesis. FEBS Lett. 356: 221-225.

Hakamatsuka, T., Mori, K., Ishida, S., Ebizuka, Y. and Sankawa, U. (1998) Purification of 2-hydroxyisoflavanone dehydratase from the cell cultures of Pueraria lobata. Phytochemistry 49: 497-505.

Hashim, M. F., Hakamatsuka, T., Ebizuka, Y. and Sankawa, U. (1990) Reaction mechanism of oxidative rearrangement of flavanone in isoflavone biosynthesis. FEBS Lett. 271: 219-222.

Heymann, E. and Mentlein, R. (1981) Carboxylesterases-amidases. Methods Enzymol. 77: 333-344.

Hosokawa, M. (2002) Multiplicity and regulatory mechanism of carboxylesterase isozymes which catalyzes the hydrolysis of long-chain fatty acid esters. Seikagaku 74: 311-316.

Humphreys, J. M. and Chapple, C. (2000) Molecular 'pharming' with plant P450s. Trends Plant Sci. 5: 271-272.

Ichinose, Y., Hisayasu, Y., Sanematsu, S., Ishiga, Y., Seki, H., Toyoda, K., Shiraishi, T. and Yamada, T. (2001) Molecular cloning and functional analysis of pea cDNA E86 encoding homologous protein to hypersensitivity-related hsr203J. Plant Sci. 160: 997-1006.

Jung, W., Yu, O., Lau, S. M., O'Keefe, D. P., Odell, J., Fader, G. and McGonigle, B. (2000) Identification and expression of isoflavone synthase, the key enzyme for biosynthesis of isoflavones in legumes. Nature Biotechnol. 18: 208-212.

Kaczor, C. M., Smith, M. W., Sangwan, I. and O'Brian, M. R. (1994) Plant d-aminolevulinic acid dehydratase. Expression in soybean root nodules and evidence for a bacterial lineage of the Alad gene. Plant Physiol. 104: 1411-1417.

Katagiri, Y., Ibrahim, R. K. and Tahara, S. (2000) HPLC analysis of white lupin isoflavonoids. Biosci. Biotechnol. Biochem. 64: 1118-1125.

Kochs, G. and Grisebach, H. (1986) Enzymic synthesis of isoflavones. Eur. J. Biochem. 155: 311-318.

Laurell, H., Contreras, J. A., Castan, I., Langin, D. and Holm, C. (2000) Analysis of the psychrotolerant property of hormone-sensitive lipase through site-directed mutagenesis. Protein Eng. 13: 711-717.

Liu, C. J., Blount, J. W., Steele, C. L. and Dixon, R. A. (2002) Bottlenecks for metabolic engineering of isoflavone glycoconjugates in Arabidopsis. Proc. Natl. Acad. Sci. USA 99: 14578-14583.

Lundqvist, T., Rice, J., Hodge, C. N., Basarab, G. S., Pierce, J. and Lindqvist, Y. (1994) Crystal structure of scytalone dehydratase—a disease determinant of the rice pathogen, Magnaporthe grisea. Structure 2: 937-944.

Manco, G., Camardella, L., Febbraio, F., Adamo, G., Carratore, V. and Rossi, M. (2000) Homology modeling and identification of serine 160 as nucleophile of the active site in a thermostable carboxylesterase from the archaeon *Archaeoglobus fulgidus*. Protein Eng. 13: 197-200.

Manco, G., Giosue, E., D'Auria, S., Herman, P., Carrea, G. and Rossi, M. (2000) Cloning, overexpression, and properties of a new thermophilic and thermostable esterase with sequence similarity to hormone-sensitive lipase subfamily from the archaeon *Archaeoglobus fulgidus*. Arch. Biochem. Biophys. 373: 182-192.

Nakamura, K., Akashi, T., Aoki, T., Kawaguchi, K. and Ayabe, S. (1999). Induction of isoflavonoid and retrochalcone branches of the flavonoid pathway in cultured Licorice echinata cells treated with yeast extract. Biosci. Biotechnol. Biochem. 63: 1618-1620.

Osterlund, T., Danielsson, B., Degerman, E., Contreras, J. A., Edgren, G., Davis, R. C., Schotz, M. C. and Holm, C. (1996) Domain-structure analysis of recombinant rat hormone-sensitive lipase. Biochem J. 319: 411-420.

Pontier, D., Godiard, L., Marco, Y. and Roby, D. (1994) hsr203J, a tobacco gene whose activation is rapid, highly localized and specific for incompatible plant/pathogen interactions. Plant J. 5: 507-521.

Sankawa, U. and Hakamatsuka, T. (1997) Biosynthesis of isoflavone and related compounds in tissue cultures of Pueraria lobata. In Dynamic aspects of natural products chemistry. Molecular biological approaches. Edited by Ogura, K. and Sankawa, U. pp. 25-48. Kodansha/Harwood Academic, Tokyo.

Satoh, T. and Hosokawa, M. (1995) Molecular aspects of carboxylesterase isoforms in comparison with other esterases. Toxicol Lett. 82/83: 439-445.

Sawada, Y., Kinoshita, K., Akashi, T., Aoki, T. and Ayabe, S. (2002) Key amino acid residues required for aryl migration catalyzed by the cytochrome P4502-hydroxyisoflavanone synthase. Plant J. 31: 555-564.

Song, W. C., Funk, C. D. and Brash, A. R. (1993) Molecular cloning of an allene oxide synthase: a cytochrome P450 specialized for the metabolism of fatty acid hydroperoxides. Proc. Natl. Acad. Sci. USA 90: 8519-8523.

Stavric, B. (1997) Chemopreventive agents in foods. In Recent Advances in Phytochemistry. Vol. 31. Functionality of Food Phytochemicals. Edited by Johns, T. and Romeo, J. T. pp. 53-87. Plenum Press, New York.

Steele, C. L., Gijzen, M., Qutob, D. and Dixon, R. A. (1999) Molecular characterization of the enzyme catalyzing the aryl migration reaction of isoflavonoid biosynthesis in soybean. Arch. Biochem. Biophys. 367: 146-150

Tada, S., Volrath, S., Guyer, D., Scheidegger, A., Ryals, J., Ohta, D. and Ward, E. (1994) Isolation and characterization of cDNAs encoding imidazole glycerol phosphate dehydratase from *Arabidopsis thaliana*. Plant Physiol. 105: 579-583.

Tronchet, M., Ranty, B., Marco, Y. and Roby, D. (2001) HSR203 antisense suppression in tobacco accelerates development of hypersensitive cell death. Plant J. 27: 115-127.

Walden, A. R., Walter, C. and Gardner, R. C. (1999) Genes expressed in *Pinus radiata* male cones include homologs to anther-specific and pathogenesis response genes. Plant Physiol. 121: 1103-1116.

Wei, Y., Contreras, J. A., Sheffield, P., Osterlund, T., Derewenda, U., Kneusel, R. E., Matern, U., Holm, C. and Derewenda, Z. S. (1999) Crystal structure of brefeldin A esterase, a bacterial homolog of the mammalian hormone-sensitive lipase. Nature Struct. Biol. 6: 340-345.

Welle, R. and Grisebach, H. (1988) Induction of phytoalexin synthesis in soybean: enzymatic cyclization of prenylated pterocarpans to glyceollin isomers. Arch. Biochem. Biophys. 263: 191-198.

Yu, O., Jung, W., Shi, J., Croes, R. A., Fader, G. M., McGonigle, B. and Odell, J. T. (2000) Production of the isoflavones genistein and daidzein in non-legume dicot and monocot tissues. Plant Physiol. 124: 781-793.

INDUSTRIAL APPLICABILITY

According to the present invention, as described above, dehydrate which plays an important role in the production step of isoflavone in a plant body is isolated, so that an amino acid sequence thereof and novel polynucleotides encoding such a sequence can be provided. Furthermore, the present invention allows the use of the gene thus obtained to the production of isoflavonoid including isoflavone.

REFERENCE TO DEPOSITED BIOLOGICAL MATERIAL (1) (a) Name and address of the depository institution to which the biological material has been deposited Name: International Patent Organism Depositary, National Institute of Advanced Industrial Science and Technology (AIST)

Address: Tsukuba Central 6, 1-1-1 Higashi, Tsukuba, Ibaraki, Japan (b) Date of deposition to the institution (a)

Mar. 20, 2003 (original deposition date)

Mar. 15, 2004 (date of transfer to the deposition based on Budapest Treaty)

(c) Accession number that the institution (a) provides for the deposition

FERM BP-08661

(2) (a) Name and address of the depository institution to which the biological material has been deposited Name: International Patent Organism Depositary, National Institute of Advanced Industrial Science and Technology (AIST)

Address: Tsukuba Central 6, 1-1-1 Higashi, Tsukuba, Ibaraki, Japan (b) Date of deposition to the institution (a)

Mar. 20, 2003 (original deposition date)

Mar. 15, 2004 (date of transfer to the deposition based on Budapest Treaty)

(c) Accession number that the institution (a) provides for the deposition

FERM BP-08662

(3) (a) Name and address of the depository institution to which the biological material has been deposited Name: International Patent Organism Depositary, National Institute of Advanced Industrial Science and Technology (AIST)

Address: Tsukuba Central 6, 1-1-1 Higashi, Tsukuba, Ibaraki, Japan (b) Date of deposition to the institution (a)

Mar. 15, 2004 (date of transfer to the deposition based on Budapest Treaty)

(c) Accession number that the institution (a) provides for the deposition

FERM BP-08663

The invention claimed is:

1. An isolated 2-hydroxyisoflavanone dehydratase, comprising the amino acid sequence of SEQ ID NO: 3 and having 2-hydroxyisoflavanone dehydratase activity.

2. The isolated 2-hydroxyisoflavanone dehydratase according to claim 1, wherein said 2-hydroxyisoflavanone dehydratase catalyzes a dehydration reaction of 2,7,4'-trihydroxyisoflavanone or 2,5,7,4'-tetrahydroxyisoflavanone to produce daidzein or genistein.

3. An isolated 2-hydroxyisoflavanone dehydratase, encoded by the polynucleotide comprising:

a nucleotide sequence encoding the 2-hydroxyisoflavanone dehydratase of claim 1 or the nucleotide sequence completely complementary thereto; or the nucleotide sequence of SEQ ID NO:4 or the nucleotide sequence completely complementary thereto, wherein said 2-hydroxyisoflavanone dehydratase has 2-hydroxyisoflavanone dehydratase activity.

* * * * *

SEQUENCE LISTING

<160> NUMBER OF SEQ ID NOS: 10

<210> SEQ ID NO 1
<211> LENGTH: 328
<212> TYPE: PRT
<213> ORGANISM: Glycyrrhiza echinata

<400> SEQUENCE: 1

```
Met Ala Ser Ser Thr Ser Thr Thr Ser Lys Glu Ile Asp Arg Glu
 1               5                  10                  15

Leu Pro Pro Leu Leu Arg Val Tyr Lys Asp Gly Thr Val Glu Arg Phe
                20                  25                  30

Leu Gly Ser Ser Phe Val Pro Ser Pro Glu Asp Pro Glu Thr Gly
            35                  40                  45

Val Ser Thr Lys Asp Ile Val Ile Ser Glu Asn Pro Thr Ile Ser Ala
        50                  55                  60

Arg Val Tyr Leu Pro Lys Leu Asn Asn Thr Thr Glu Lys Leu Pro Ile
 65                 70                  75                  80

Leu Val Tyr Tyr His Gly Gly Ala Phe Cys Leu Glu Ser Ala Phe Ser
                85                  90                  95

Phe Leu His Gln Arg Tyr Leu Asn Ile Val Ala Ser Lys Ala Asn Val
            100                 105                 110

Leu Val Val Ser Ile Glu Tyr Arg Leu Ala Pro Glu His Pro Leu Pro
        115                 120                 125

Ala Ala Tyr Glu Asp Gly Trp Tyr Ala Leu Lys Trp Val Thr Ser His
    130                 135                 140

Ser Thr Asn Asn Asn Lys Pro Thr Asn Ala Asp Pro Trp Leu Ile Lys
145                 150                 155                 160

His Gly Asp Phe Asn Arg Phe Tyr Ile Gly Gly Asp Thr Ser Gly Ala
                165                 170                 175

Asn Ile Ala His Asn Ala Ala Leu Arg Val Gly Ala Glu Ala Leu Pro
            180                 185                 190

Gly Gly Leu Arg Ile Ala Gly Val Leu Ser Ala Phe Pro Leu Phe Trp
        195                 200                 205

Gly Ser Lys Pro Val Leu Ser Glu Pro Val Glu Gly His Glu Lys Ser
    210                 215                 220

Ser Pro Met Gln Val Trp Asn Phe Val Tyr Pro Asp Ala Pro Gly Gly
225                 230                 235                 240

Ile Asp Asn Pro Leu Ile Asn Pro Leu Ala Pro Gly Ala Pro Asn Leu
                245                 250                 255

Ala Thr Leu Gly Cys Pro Lys Met Leu Val Phe Val Ala Gly Lys Asp
            260                 265                 270

Asp Leu Arg Asp Arg Gly Ile Trp Tyr Tyr Glu Ala Val Lys Glu Ser
        275                 280                 285

Gly Trp Lys Gly Asp Val Glu Leu Ala Gln Tyr Glu Gly Glu Glu His
    290                 295                 300

Cys Phe Gln Ile Tyr His Pro Glu Thr Glu Asn Ser Lys Asp Leu Ile
305                 310                 315                 320

Gly Arg Ile Ala Ser Phe Leu Val
                325
```

<210> SEQ ID NO 2
<211> LENGTH: 1178
<212> TYPE: DNA

<213> ORGANISM: Glycyrrhiza echinata
<220> FEATURE:
<221> NAME/KEY: CDS
<222> LOCATION: (23)..(1006)

<400> SEQUENCE: 2

```
ctattccatt cttttccgtt ca atg gct tct tca acc tca aca acc act tcc        52
                        Met Ala Ser Ser Thr Ser Thr Thr Thr Ser
                        1               5                   10 aaa gag ata gac agg gag ctt cct cct ctt ctc cgg gtc tac aaa gat        100
Lys Glu Ile Asp Arg Glu Leu Pro Pro Leu Leu Arg Val Tyr Lys Asp
             15                  20                  25 gga acc gtg gag cga ttc cta ggc tca tcg ttt gta cca cct tcc cct        148
Gly Thr Val Glu Arg Phe Leu Gly Ser Ser Phe Val Pro Pro Ser Pro
         30                  35                  40 gaa gac ccc gaa aca ggg gtt tcc acg aaa gac ata gta atc tca gaa        196
Glu Asp Pro Glu Thr Gly Val Ser Thr Lys Asp Ile Val Ile Ser Glu
     45                  50                  55 aac ccc acc atc tct gct cgc gtt tac ctt cca aaa ctg aac aac acc        244
Asn Pro Thr Ile Ser Ala Arg Val Tyr Leu Pro Lys Leu Asn Asn Thr
 60                  65                  70 acc gag aag ctc cca atc ttg gtc tac tac cac ggc ggc gcg ttc tgc        292
Thr Glu Lys Leu Pro Ile Leu Val Tyr Tyr His Gly Gly Ala Phe Cys
75                  80                  85                  90 ctc gaa tct gct ttc tcc ttc ctc cac caa cgc tac ctc aac atc gtt        340
Leu Glu Ser Ala Phe Ser Phe Leu His Gln Arg Tyr Leu Asn Ile Val
                 95                 100                 105 gct tcc aag gca aat gtt cta gta gtt tcc atc gag tac agg ctc gcc        388
Ala Ser Lys Ala Asn Val Leu Val Val Ser Ile Glu Tyr Arg Leu Ala
            110                 115                 120 cca gaa cac cct ctt ccg gct gca tat gaa gat ggt tgg tat gct ctc        436
Pro Glu His Pro Leu Pro Ala Ala Tyr Glu Asp Gly Trp Tyr Ala Leu
        125                 130                 135 aaa tgg gtc act tct cat tcc aca aac aac aac aaa ccc acc aac gct        484
Lys Trp Val Thr Ser His Ser Thr Asn Asn Asn Lys Pro Thr Asn Ala
140                 145                 150 gac cca tgg ttg atc aaa cac ggt gat ttc aac agg ttc tac atc ggg        532
Asp Pro Trp Leu Ile Lys His Gly Asp Phe Asn Arg Phe Tyr Ile Gly
155                 160                 165                 170 ggt gac act tct ggt gca aac att gca cac aat gcg gct ctt cgt gtt        580
Gly Asp Thr Ser Gly Ala Asn Ile Ala His Asn Ala Ala Leu Arg Val
                175                 180                 185 ggt gct gag gcc tta cct ggg ggg ctg aga ata gca ggg gta ctc tct        628
Gly Ala Glu Ala Leu Pro Gly Gly Leu Arg Ile Ala Gly Val Leu Ser
            190                 195                 200 gct ttt cct ctg ttt tgg ggt tct aag cct gtt ttg tca gaa cct gtc        676
Ala Phe Pro Leu Phe Trp Gly Ser Lys Pro Val Leu Ser Glu Pro Val
        205                 210                 215 gag ggg cat gag aag agc tca ccc atg caa gtt tgg aac ttt gtg tac        724
Glu Gly His Glu Lys Ser Ser Pro Met Gln Val Trp Asn Phe Val Tyr
    220                 225                 230 cca gat gca cca ggt ggc ata gat aac cca cta atc aac cct ttg gca        772
Pro Asp Ala Pro Gly Gly Ile Asp Asn Pro Leu Ile Asn Pro Leu Ala
235                 240                 245                 250 cct ggg gct cct aac ttg gcc aca ctt ggg tgt cca aag atg ttg gtc        820
Pro Gly Ala Pro Asn Leu Ala Thr Leu Gly Cys Pro Lys Met Leu Val
                255                 260                 265 ttt gtt gcg ggg aag gat gat ctt aga gac aga ggg att tgg tac tat        868
Phe Val Ala Gly Lys Asp Asp Leu Arg Asp Arg Gly Ile Trp Tyr Tyr
            270                 275                 280
```

-continued

```
gag gct gtg aag gaa agt ggg tgg aaa ggg gat gtg gaa ctt gct cag       916
Glu Ala Val Lys Glu Ser Gly Trp Lys Gly Asp Val Glu Leu Ala Gln
        285                 290                 295 tat gaa ggg gag gaa cat tgc ttc cag atc tac cat cct gaa act gag       964
Tyr Glu Gly Glu Glu His Cys Phe Gln Ile Tyr His Pro Glu Thr Glu
300                 305                 310 aat tct aaa gat ctc atc ggt cgc atc gct tcc ttc ctt gtt              1006
Asn Ser Lys Asp Leu Ile Gly Arg Ile Ala Ser Phe Leu Val
315                 320                 325 tgaacacaca gctagacttc gggttcatta ttactagtat gtgatttgt ttgattaatg     1066 ttttgtcatc aattgatggg taataaattg gattagggta ctagggttcc tgaatcatgc    1126
tcaattttac ttttcctgta ctattacttg tttatgaaag aattaatggc at            1178
```

<210> SEQ ID NO 3
<211> LENGTH: 319
<212> TYPE: PRT
<213> ORGANISM: Glycine max

<400> SEQUENCE: 3

```
Met Ala Lys Glu Ile Val Lys Glu Leu Leu Pro Leu Ile Arg Val Tyr
  1               5                  10                  15

Lys Asp Gly Ser Val Glu Arg Leu Leu Ser Ser Glu Asn Val Ala Ala
             20                  25                  30

Ser Pro Glu Asp Pro Gln Thr Gly Val Ser Ser Lys Asp Ile Val Ile
         35                  40                  45

Ala Asp Asn Pro Tyr Val Ser Ala Arg Ile Phe Leu Pro Lys Ser His
     50                  55                  60

His Thr Asn Asn Lys Leu Pro Ile Phe Leu Tyr Phe His Gly Gly Ala
 65                  70                  75                  80

Phe Cys Val Glu Ser Ala Phe Ser Phe Phe Val His Arg Tyr Leu Asn
                 85                  90                  95

Ile Leu Ala Ser Glu Ala Asn Ile Ala Ile Ser Val Asp Phe Arg
             100                 105                 110

Leu Leu Pro His His Pro Ile Pro Ala Ala Tyr Glu Asp Gly Trp Thr
         115                 120                 125

Thr Leu Lys Trp Ile Ala Ser His Ala Asn Asn Thr Asn Thr Thr Asn
    130                 135                 140

Pro Glu Pro Trp Leu Leu Asn His Ala Asp Phe Thr Lys Val Tyr Val
145                 150                 155                 160

Gly Gly Glu Thr Ser Gly Ala Asn Ile Ala His Asn Leu Leu Leu Arg
                165                 170                 175

Ala Gly Asn Glu Ser Leu Pro Gly Asp Leu Lys Ile Leu Gly Gly Leu
            180                 185                 190

Leu Cys Cys Pro Phe Phe Trp Gly Ser Lys Pro Ile Gly Ser Glu Ala
        195                 200                 205

Val Glu Gly His Glu Gln Ser Leu Ala Met Lys Val Trp Asn Phe Ala
    210                 215                 220

Cys Pro Asp Ala Pro Gly Gly Ile Asp Asn Pro Trp Ile Asn Pro Cys
225                 230                 235                 240

Val Pro Gly Ala Pro Ser Leu Ala Thr Leu Ala Cys Ser Lys Leu Leu
                245                 250                 255

Val Thr Ile Thr Gly Lys Asp Glu Phe Arg Asp Arg Asp Ile Leu Tyr
            260                 265                 270

His His Thr Val Glu Gln Ser Gly Trp Gln Gly Glu Leu Gln Leu Phe
        275                 280                 285
```

-continued

```
Asp Ala Gly Asp Glu Glu His Ala Phe Gln Leu Phe Lys Pro Glu Thr
    290                 295                 300

His Leu Ala Lys Ala Met Ile Lys Arg Leu Ala Ser Phe Leu Val
305                 310                 315

<210> SEQ ID NO 4
<211> LENGTH: 960
<212> TYPE: DNA
<213> ORGANISM: Glycine max
<220> FEATURE:
<221> NAME/KEY: CDS
<222> LOCATION: (1)..(957)

<400> SEQUENCE: 4 atg gcg aag gag ata gtg aaa gag ctt ctt cct cta att cga gtg tac        48
Met Ala Lys Glu Ile Val Lys Glu Leu Leu Pro Leu Ile Arg Val Tyr
  1               5                  10                  15 aag gat ggc agc gtg gag cgt ctt cta agc tct gaa aac gtg gca gcc        96
Lys Asp Gly Ser Val Glu Arg Leu Leu Ser Ser Glu Asn Val Ala Ala
             20                  25                  30 tcc cct gaa gat ccc caa act gga gtc tca tcc aaa gac ata gtc atc       144
Ser Pro Glu Asp Pro Gln Thr Gly Val Ser Ser Lys Asp Ile Val Ile
         35                  40                  45 gca gac aac ccc tac gtc tcc gct cgc att ttc ctt ccc aaa tcc cac       192
Ala Asp Asn Pro Tyr Val Ser Ala Arg Ile Phe Leu Pro Lys Ser His
     50                  55                  60 cac act aac aac aaa ctc ccc atc ttc ctc tac ttc cac ggt ggc gcc       240
His Thr Asn Asn Lys Leu Pro Ile Phe Leu Tyr Phe His Gly Gly Ala
 65                  70                  75                  80 ttt tgc gtc gaa tcc gcc ttc tcc ttt ttc gtc cac cgc tat ctc aac       288
Phe Cys Val Glu Ser Ala Phe Ser Phe Phe Val His Arg Tyr Leu Asn
                 85                  90                  95 atc ttg gcc tca gaa gcc aac ata ata gcc atc tcc gtc gac ttc aga       336
Ile Leu Ala Ser Glu Ala Asn Ile Ile Ala Ile Ser Val Asp Phe Arg
            100                 105                 110 ctc ctc cca cac cac cct atc cct gct gcc tac gaa gac ggt tgg acc       384
Leu Leu Pro His His Pro Ile Pro Ala Ala Tyr Glu Asp Gly Trp Thr
        115                 120                 125 acc ctc aaa tgg att gct tcc cac gcc aac aac acc aac acc acc aac       432
Thr Leu Lys Trp Ile Ala Ser His Ala Asn Asn Thr Asn Thr Thr Asn
    130                 135                 140 ccg gag cca tgg cta ctc aac cac gcc gac ttc acc aaa gtc tac gta       480
Pro Glu Pro Trp Leu Leu Asn His Ala Asp Phe Thr Lys Val Tyr Val
145                 150                 155                 160 gga ggt gaa acc agc ggt gct aac atc gca cac aac ctg ctt ttg cgt       528
Gly Gly Glu Thr Ser Gly Ala Asn Ile Ala His Asn Leu Leu Leu Arg
                165                 170                 175 gca ggt aac gaa tcc ctc ccc ggg gat ctg aaa ata ttg ggt gga tta       576
Ala Gly Asn Glu Ser Leu Pro Gly Asp Leu Lys Ile Leu Gly Gly Leu
            180                 185                 190 cta tgc tgc ccc ttc ttc tgg ggc tcg aag cca att ggg tcg gag gct       624
Leu Cys Cys Pro Phe Phe Trp Gly Ser Lys Pro Ile Gly Ser Glu Ala
        195                 200                 205 gtt gag ggg cac gag cag agt ttg gcc atg aag gtc tgg aac ttt gcc       672
Val Glu Gly His Glu Gln Ser Leu Ala Met Lys Val Trp Asn Phe Ala
    210                 215                 220 tgc cct gat gcc ccc ggt gga atc gat aac ccc tgg atc aac ccc tgt       720
Cys Pro Asp Ala Pro Gly Gly Ile Asp Asn Pro Trp Ile Asn Pro Cys
225                 230                 235                 240 gtt cct ggg gca ccc tct ttg gcc act ctt gcc tgc tct aag ttg ctc       768
Val Pro Gly Ala Pro Ser Leu Ala Thr Leu Ala Cys Ser Lys Leu Leu
```

```
Val Pro Gly Ala Pro Ser Leu Ala Thr Leu Ala Cys Ser Lys Leu Leu
            245                 250                 255 gtt act atc act ggc aaa gac gag ttc aga gac aga gat att ctc tac      816
Val Thr Ile Thr Gly Lys Asp Glu Phe Arg Asp Arg Asp Ile Leu Tyr
            260                 265                 270 cac cac acc gtt gag caa agt ggc tgg caa ggt gaa ctt caa ctc ttt      864
His His Thr Val Glu Gln Ser Gly Trp Gln Gly Glu Leu Gln Leu Phe
        275                 280                 285 gat gct ggc gat gag gag cat gct ttc cag ctc ttc aag cct gag act      912
Asp Ala Gly Asp Glu Glu His Ala Phe Gln Leu Phe Lys Pro Glu Thr
    290                 295                 300 cat ctt gct aaa gcc atg atc aaa cgc ttg gct tct ttt ctg gtt tga      960
His Leu Ala Lys Ala Met Ile Lys Arg Leu Ala Ser Phe Leu Val
305                 310                 315

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtcatatggc gaaggagata gtgaa                                           25

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agggatccat caaaccagaa aaga                                            24

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtcatatggc ttcttcaacc tcaac                                           25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctggatcctc aaacaaggaa ggaag                                           25

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 9
ggggcccgga tccacggcga aggagatagt gaaag                    35

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggagctcga gtcaaaccag aaaagaagcc                          30
```